United States Patent
Deur-Bert et al.

(10) Patent No.: US 10,590,052 B2
(45) Date of Patent: Mar. 17, 2020

(54) AZEOTROPIC COMPOSITIONS OF HYDROGEN FLUORIDE AND Z-3,3,3-TRIFLUORO-1-CHLOROPROPENE

(71) Applicant: ARKEMA FRANCE, Colombes (FR)

(72) Inventors: Dominique Deur-Bert, Charly (FR); Anne Pigamo, Francheville (FR); Philippe Bonnet, Lyons (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/018,191

(22) Filed: Jun. 26, 2018

(65) Prior Publication Data

US 2018/0297919 A1 Oct. 18, 2018

Related U.S. Application Data

(62) Division of application No. 15/104,836, filed as application No. PCT/FR2014/053228 on Dec. 9, 2014, now Pat. No. 10,029,961.

(30) Foreign Application Priority Data

Dec. 19, 2013 (FR) ..................... 13.62982

(51) Int. Cl.
- *C07C 17/383* (2006.01)
- *B01D 3/36* (2006.01)
- *C07C 19/08* (2006.01)
- *C07C 21/18* (2006.01)
- *C01B 7/19* (2006.01)

(52) U.S. Cl.
CPC .............. *C07C 17/383* (2013.01); *B01D 3/36* (2013.01); *C01B 7/191* (2013.01); *C07C 19/08* (2013.01); *C07C 21/18* (2013.01); *C07B 2200/09* (2013.01)

(58) Field of Classification Search
CPC ....... C07C 17/06; C07C 17/10; C07C 17/206; C07C 17/25; C07C 17/358; C07C 17/383; C07C 21/18
See application file for complete search history.

(56) References Cited

U.S. PATENT DOCUMENTS

| | | | |
|---|---|---|---|
| 6,013,846 A | 1/2000 | Wismer et al. | |
| 6,328,907 B1 | 12/2001 | Nakada et al. | |
| 7,183,448 B2 | 2/2007 | Nakada et al. | |
| 7,423,188 B2 | 9/2008 | Miller et al. | |
| 8,075,797 B2 | 12/2011 | Hulse et al. | |
| 8,273,928 B2 | 9/2012 | Knapp | |
| 8,378,158 B2 | 2/2013 | Hulse et al. | |
| 8,450,537 B2 | 5/2013 | Rao et al. | |
| 8,858,823 B2 | 10/2014 | Rached | |
| 9,000,238 B2 | 4/2015 | Knapp | |
| 9,889,416 B2 | 2/2018 | Bonnet et al. | |
| 10,029,961 B2 | 7/2018 | Deur-Bert et al. | |
| 10,029,963 B2 | 7/2018 | Bonnet et al. | |
| 10,077,221 B2 | 9/2018 | Bonnet et al. | |
| 10,252,913 B2 | 4/2019 | Bonnet et al. | |
| 10,266,465 B2 | 4/2019 | Bonnet et al. | |
| 10,343,963 B2 | 7/2019 | Bonnet et al. | |
| 2007/0100173 A1 | 5/2007 | Miller et al. | |
| 2007/0100175 A1 | 5/2007 | Miller et al. | |
| 2008/0051612 A1 | 2/2008 | Knapp et al. | |
| 2009/0127496 A1 | 5/2009 | Rao et al. | |
| 2010/0072415 A1 | 3/2010 | Rao | |
| 2010/0187088 A1 | 7/2010 | Merkel et al. | |
| 2010/0237279 A1 | 9/2010 | Hulse et al. | |
| 2011/0112340 A1 | 5/2011 | Smith et al. | |
| 2011/0218369 A1 | 9/2011 | Elsheikh et al. | |
| 2011/0218370 A1* | 9/2011 | Elsheikh | C07C 17/06 570/236 |
| 2012/0010449 A1* | 1/2012 | Wismer | C01B 7/0712 570/178 |
| 2012/0041239 A1 | 2/2012 | Suzuki et al. | |
| 2012/0053369 A1 | 3/2012 | Hulse et al. | |
| 2012/0053372 A1 | 3/2012 | Hulse et al. | |
| 2012/0056122 A1 | 3/2012 | Hulse et al. | |
| 2012/0138841 A1 | 6/2012 | Hulse et al. | |
| 2012/0222448 A1 | 9/2012 | Chaki et al. | |
| 2012/0305382 A1 | 12/2012 | Knapp | |
| 2013/0105296 A1 | 5/2013 | Chaki et al. | |
| 2014/0012052 A1 | 1/2014 | Pham et al. | |
| 2014/0024575 A1 | 1/2014 | Rached | |
| 2015/0105596 A1 | 4/2015 | Wang | |
| 2015/0197467 A1 | 7/2015 | Pigamo et al. | |
| 2016/0009555 A1 | 1/2016 | Bonnet et al. | |
| 2016/0023176 A1 | 1/2016 | Bonnet et al. | |
| 2016/0023974 A1 | 1/2016 | Bonnet et al. | |
| 2016/0031773 A1 | 2/2016 | Bonnet et al. | |
| 2016/0046548 A1 | 2/2016 | Bonnet et al. | |

(Continued)

FOREIGN PATENT DOCUMENTS

JP H11-279088 A 10/1999
JP 2012-516336 A 7/2012

(Continued)

OTHER PUBLICATIONS

Notification of Reasons for Refusal issued by the Japanese Intellectual Property Office in JP Patent Application No. 2016-541417, dated Sep. 6, 2018; and English-language translation thereof, 7 pages.

(Continued)

*Primary Examiner* — Jafar F Parsa
(74) *Attorney, Agent, or Firm* — Buchanan Ingersoll & Rooney P.C.

(57) ABSTRACT

A process for producing a main (hydro)halocarbon compound, including the formation of a mixture of compounds including hydrogen fluoride, Z-3,3,3-trifluoro-1-chloropropene and one or more other (hydro)halocarbon compounds, distillation of this mixture making it possible to collect, firstly, an azeotropic composition, and, secondly, at least one of the compounds of the mixture. The (hydro)halocarbon compounds are preferably selected among tetrachlorofluoropropanes, trichlorodifluoropropanes, dichlorotrifluoropropanes, chlorotetrafluoropropanes, pentafluoropropanes, dichlorodifluoropropenes, chlorotrifluoropropenes and tetrafluoropropenes.

11 Claims, 4 Drawing Sheets

(56) References Cited

U.S. PATENT DOCUMENTS

| | | |
|---|---|---|
| 2017/0297982 A1 | 10/2017 | Deur-Bert et al. |
| 2018/0126348 A1 | 5/2018 | Bonnet et al. |
| 2018/0312453 A1 | 11/2018 | Bonnet et al. |
| 2018/0354875 A1 | 12/2018 | Bonnet et al. |

FOREIGN PATENT DOCUMENTS

| | | |
|---|---|---|
| JP | 2012-521430 A | 9/2012 |
| WO | WO 97/27163 A1 | 7/1997 |
| WO | WO 00/29361 A1 | 5/2000 |
| WO | WO 2007/053736 A2 | 5/2007 |
| WO | WO 2008/002500 A1 | 1/2008 |
| WO | WO 2009/105517 A2 | 8/2009 |
| WO | WO 2010/059493 A1 | 5/2010 |
| WO | WO 2010/088196 A2 | 8/2010 |
| WO | WO 2010/088196 A3 | 8/2010 |
| WO | WO 2010/111067 A1 | 9/2010 |
| WO | WO 2012/075283 A2 | 6/2012 |
| WO | WO 2014/147310 A1 | 9/2014 |
| WO | WO 2014/147311 A1 | 9/2014 |
| WO | WO 2014/147312 A1 | 9/2014 |
| WO | WO 2014/147313 A1 | 9/2014 |
| WO | WO 2014/147314 A1 | 9/2014 |

OTHER PUBLICATIONS

International Search Report (PCT/ISA/210) dated Mar. 20, 2015, by the European Patent Office as the International Searching Authority for International Application No. PCT/FR2014/053228.

Written Opinion (PCT/ISA/237) dated Mar. 10, 2015, by the European Patent Office as the International Searching Authority for International Application No. PCT/FR2014/053228.

* cited by examiner

AZEOTROPIC COMPOSITIONS OF HYDROGEN FLUORIDE AND Z-3,3,3-TRIFLUORO-1-CHLOROPROPENE

CROSS REFERENCE TO RELATED APPLICATIONS

The present application is a divisional of U.S. application Ser. No. 15/104,836, filed on Jun. 15, 2016, which is a U.S. national stage of International Application No. PCT/FR2014/053228, filed on Dec. 9, 2014, which claims the benefit of French Application No. 13.62982, filed on Dec. 19, 2013. The entire contents of each of U.S. application Ser. No. 15/104,836, International Application No. PCT/FR2014/053228, and French Application No. 13.62982 are hereby incorporated herein by reference in their entirety.

TECHNICAL FIELD

The present invention relates to azeotropic or quasi-azeotropic compositions based on hydrogen fluoride and Z-3,3,3-trifluoro-1-chloropropene.

TECHNICAL BACKGROUND 3,3,3-Trifluoro-1-chloropropene, also known as 1-chloro-3,3,3-trifluoropropene (HCFO-1233zd), exists in the form of two isomers: the cis isomer, namely Z-3,3,3-trifluoro-1-chloropropene (HCFO-1233zdZ), and the trans isomer, namely E-3,3,3-trifluoro-1-chloropropene (HCFO-1233zdE). They have different boiling points: 18.5° C. for the trans compound and 39.5° C. for the cis compound, respectively.

Fluids based on E-3,3,3-trifluoro-1-chloropropene (HCFO-1233zdE) have found numerous applications in varied industrial fields, especially as heat-transfer fluids, propellants, foaming agents, swelling agents, gaseous dielectrics, polymerization media or monomers, support fluids, abrasives, drying agents and fluids for power production units.

The manufacture of HCFO-1233zdE is accompanied by a multitude of by-products, having a boiling point close to HCFO-1233zdE. This leads to quite complex and expensive purification steps. The difficulties encountered during the purification of HCFO-1233zdE generally entail a consequent loss of the desired product. Furthermore, the by-products may form azeotropic compositions with HCFO-1233zdE, making separation by simple distillation very difficult or even impossible.

U.S. Pat. No. 6,013,846 describes an azeotropic composition of HCFO-1233zd and hydrogen fluoride (HF). The document does not mention the isomeric form of HCFO-1233zd.

U.S. Pat. No. 6,328,907 describes an azeotropic composition of 1,1,1,3,3-pentafluoropropane (HFC-245fa) and HF.

U.S. Pat. No. 8,378,158 describes a quasi-azeotropic composition of HCFO-1233zdZ and HF.

U.S. Pat. No. 7,423,188 describes an azeotropic composition of E-1,3,3,3-tetrafluoropropene (HFO-1234zeE) and HF.

WO 2008/002500 describes an azeotropic composition of Z-1,3,3,3-tetrafluoropropene (HFO-1234zeZ) and HF.

U.S. Pat. No. 7,183,448 describes an azeotropic composition of HFC-245fa and HCFO-1233zd. It is pointed out in the document that the azeotrope is obtained with the trans isomer of HCFO-1233zd.

U.S. Pat. No. 8,075,797 describes a quasi-azeotropic composition of HF, HFC-245fa and HCFO-1233zd. It is pointed out in the document that the quasi-azeotrope is obtained with the—trans isomer of HCFO-1233zd.

There is still a need to provide other azeotropic compositions and especially azeotropic compositions based on compounds that can participate in the manufacture of HCFO-1233zdE. However, in general, azeotropes are difficult to predict.

SUMMARY OF THE INVENTION

The invention relates firstly to an azeotropic or quasi-azeotropic composition comprising hydrogen fluoride, Z-3,3,3-trifluoro-1-chloropropene and one or more (hydro)halocarbon compounds comprising from 1 to 3 carbon atoms.

According to one embodiment, the (hydro)halocarbon compound(s) comprise three carbon atoms, and are preferably chosen from propanes and propenes that are partially or totally substituted with halogens.

According to one embodiment, the (hydro)halocarbon compound(s) are chosen from tetrachlorofluoropropanes, trichlorodifluoropropanes, dichlorotrifluoropropanes, chlorotetrafluoropropanes, pentafluoropropanes, trichlorofluoropropenes, dichlorodifluoropropenes, chlorotrifluoropropenes and tetrafluoropropenes.

According to one embodiment, the composition of the invention comprises hydrogen fluoride, Z-3,3,3-trifluoro-1-chloropropene, E-3,3,3-trifluoro-1-chloropropene and one or more other (hydro)halocarbon compounds comprising from 1 to 3 carbon atoms.

According to one embodiment, the composition of the invention comprises hydrogen fluoride, Z-3,3,3-trifluoro-1-chloropropene, E-1,3,3,3-tetrafluoropropene and one or more other (hydro)halocarbon compounds comprising from 1 to 3 carbon atoms.

According to one embodiment, the composition of the invention comprises hydrogen fluoride, Z-3,3,3-trifluoro-1-chloropropene, Z-1,3,3,3-tetrafluoropropene and one or more other (hydro)halocarbon compounds comprising from 1 to 3 carbon atoms.

According to one embodiment, the composition of the invention comprises hydrogen fluoride, Z-3,3,3-trifluoro-1-chloropropene, 1,1,1,3,3-pentafluoropropane and one or more other (hydro)halocarbon compounds comprising from 1 to 3 carbon atoms.

According to one embodiment, the composition of the invention is a ternary mixture, and is preferably a mixture of hydrogen fluoride, Z-3,3,3-trifluoro-1-chloropropene and E-3,3,3-trifluoro-1-chloropropene.

According to one embodiment, the composition of the invention is a quaternary mixture, and is preferably a mixture of:
- hydrogen fluoride, Z-3,3,3-trifluoro-1-chloropropene, E-3,3,3-trifluoro-1-chloropropene and 1,1,1,3,3-pentafluoropropane; or
- hydrogen fluoride, Z-3,3,3-trifluoro-1-chloropropene, E-1,3,3,3-tetrafluoropropene and 1,1,1,3,3-pentafluoropropane; or
- hydrogen fluoride, Z-3,3,3-trifluoro-1-chloropropene, Z-1,3,3,3-tetrafluoropropene and 1,1,1,3,3-pentafluoropropane.

According to one embodiment, the composition of the invention is a quinternary mixture, and is preferably a mixture of:

hydrogen fluoride, Z-3,3,3-trifluoro-1-chloropropene, E-3,3,3-trifluoro-1-chloropropene, Z 1,3,3,3-tetrafluoropropene and 1,1,1,3,3-pentafluoropropane; or hydrogen fluoride, Z-3,3,3-trifluoro-1-chloropropene, E-3,3,3-trifluoro-1-chloropropene, E 1,3,3,3-tetrafluoropropene and 1,1,1,3,3-pentafluoropropane; or hydrogen fluoride, Z-3,3,3-trifluoro-1-chloropropene, Z-1,3,3,3-tetrafluoropropene, E-1,3,3,3-tetrafluoropropene and 1,1,1,3,3-pentafluoropropane.

According to one embodiment, the composition of the invention is a senary mixture, and is preferably a mixture of:

hydrogen fluoride, Z-3,3,3-trifluoro-1-chloropropene, E-3,3,3-trifluoro-1-chloropropene, Z-1,3,3,3-tetrafluoropropene, E-1,3,3,3-tetrafluoropropene and 1,1,1,3,3-pentafluoropropane.

According to one embodiment, the composition according to the invention is hetero-azeotropic or quasi-hetero-azeotropic.

According to one embodiment, the composition of the invention comprises from 1% to 85% by weight, preferably from 1% to 80% by weight, more particularly preferably from 5% to 80% by weight and most particularly preferably from 5% to 75% by weight of hydrogen fluoride; and/or from 15% to 99% by weight, preferably from 20% to 99% by weight, more particularly preferably from 20% to 95% by weight and most particularly preferably from 25% to 95% by weight of (hydro)halocarbon compounds comprising from 1 to 3 carbon atoms.

According to one embodiment, the composition of the invention has a boiling point of 0 to 40° C. for a pressure from 0.5 to 9 bar absolute.

The invention also relates to a process for producing a main (hydro)halocarbon compound, comprising:

the formation of a mixture of compounds comprising hydrogen fluoride, Z-3,3,3-trifluoro-1-chloropropene and one or more other (hydro)halocarbon compounds;

distillation of this mixture making it possible to collect, firstly, an azeotropic composition of the invention, and, secondly, at least one of the compounds of the mixture.

According to one embodiment, distillation makes it possible to collect, firstly, an azeotropic composition of the invention, and, secondly, hydrogen fluoride; or alternatively, firstly, an azeotropic composition of the invention, and, secondly, E-3,3,3-trifluoro-1-chloropropene.

According to one embodiment, the process of the invention is a process for producing 3,3,3-trifluoro-1-chloropropene, and preferably E-3,3,3-trifluoro-1-chloropropene.

According to one embodiment, the mixture of compounds is obtained after a fluorination step, comprising the reaction of a chloro compound with hydrogen fluoride.

According to one embodiment, the azeotropic composition collected is separated, preferably by decantation, into two immiscible liquid fractions, namely a fraction rich in hydrogen fluoride and a fraction poor in hydrogen fluoride, the fraction rich in hydrogen fluoride containing a higher proportion of hydrogen fluoride than the fraction poor in hydrogen fluoride; and the fraction rich in hydrogen fluoride being, where appropriate, recycled into the fluorination step. The fraction poor in hydrogen fluoride may undergo distillation to allow the collection, firstly, of an azeotropic composition of the invention and, secondly, of E-3,3,3-trifluoro-1-chloropropene.

According to one embodiment, the starting chloro compound that reacts with hydrogen fluoride is 1,1,1,3,3-pentachloropropane or 1,1,3,3-tetrachloropropene.

The present invention makes it possible to satisfy the need expressed above. It more particularly provides azeotropic or quasi-azeotropic compositions from compounds that can participate in the manufacture of various (hydro)halocarbon compounds, and especially in the manufacture of HCFO-1233zdE.

Identification of these azeotropic or quasi-azeotropic compositions thus makes it possible especially to improve the efficiency and performance of processes for producing (hydro)halocarbon compounds, and especially for producing HCFO-1233zdE.

In a preferred embodiment, these compositions are hetero-azeotropic, i.e. they are compositions whose condensed liquid forms two immiscible solutions that may be readily separated, for example by decantation. This entails a considerable advantage for the envisaged purification operations.

Figure 1:
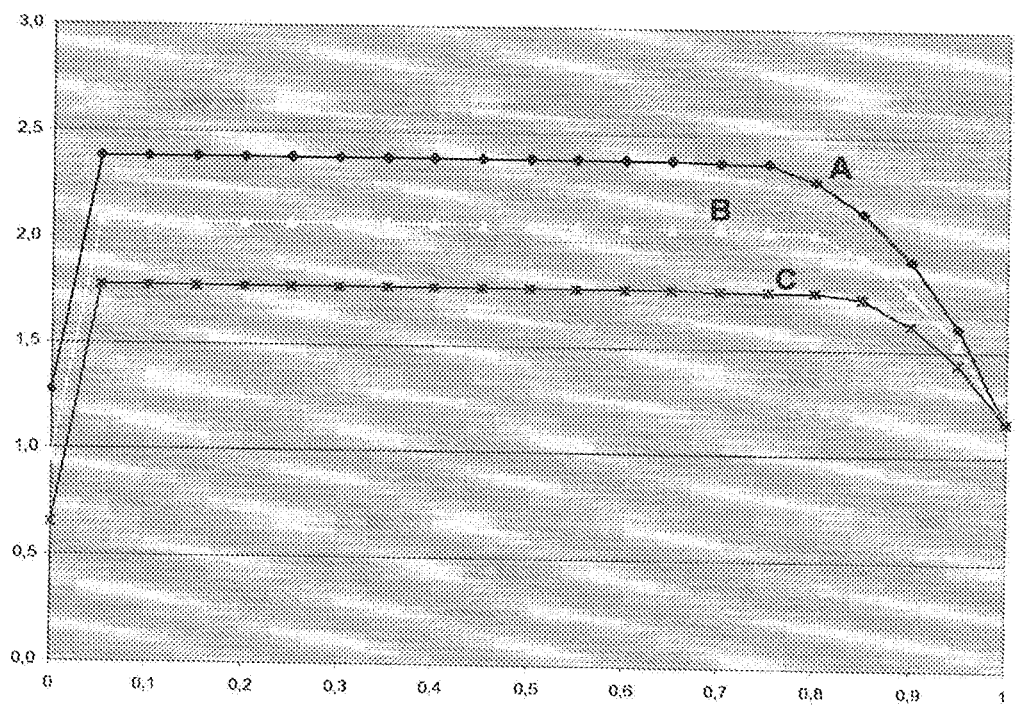
FIG. 1 represents the vapor pressure (on the y-axis, in bar absolute) of mixtures according to the invention in accordance with Example 1, for the 25° C. isotherm. The mass fraction of HF in the composition is given on the x-axis. Curves A, B and C correspond to various compositions of (hydro)halocarbon compounds (see Example 1).

Curves A, B, C, D, E and F correspond to various compositions of (hydro)halocarbon compounds (see Example 8).

DESCRIPTION OF EMBODIMENTS OF THE INVENTION

The invention is now described in greater detail and in a nonlimiting manner in the description that follows.

Unless otherwise mentioned, all proportions mentioned in the present patent application are mass proportions.

The invention provides azeotropic, quasi-azeotropic, hetero-azeotropic and quasi-hetero-azeotropic compositions.

A mixture is considered as azeotropic when the pressure at the dew point is equal to that at the bubble formation point, which means that the composition of the vapor is equal to that of the condensed liquid.

A mixture is considered as quasi-azeotropic when the pressure at the dew point is substantially equal to that at the bubble formation point, which means that the vapor composition is substantially equal to that of the condensed liquid: for example, the pressure difference between the pressure at the dew point and the pressure at the bubble formation point is less than or equal to 5% on the basis of the pressure at the bubble formation point.

A hetero-azeotropic mixture is an azeotropic mixture whose condensed liquid forms two immiscible solutions that may be readily separated, for example by decantation.

A quasi-hetero-azeotropic mixture is a quasi-azeotropic mixture whose condensed liquid forms two immiscible solutions that may be readily separated, for example by decantation.

The compositions according to the invention comprise HF, HCFO-1233zdZ and one or more (hydro)halocarbon compounds comprising from 1 to 3 carbon atoms.

(Hydro)halocarbon compounds are compounds based on carbon, halogen and optionally hydrogen atoms; advantageously, they are compounds based on carbon, chlorine and/or fluorine and optionally hydrogen atoms. They are advantageously alkanes or alkenes that are partially or totally substituted with halogen atoms, especially chlorine and/or fluorine.

According to a particular embodiment, the (hydro)halocarbon compounds that may be used in the context of the invention comprise 1 or 2 carbon atoms.

They may be chosen especially from:
chloromethane (HCC-40);
chloropentafluoroethane (HCFC-115);
chlorotetrafluoroethane (HFCF-124), namely 1-chloro-1,2,2,2-tetrafluoroethane and 1-chloro-1,1,2,2-tetrafluoroethane;
pentafluoroethane (HFC-125);
chlorotrifluoroethane, namely, in particular 1-chloro-1,2,2-trifluoroethane (HCFC-133), 1-chloro-2,2,2-trifluoroethane (HCFC-133a) and 1-chloro-1,1,2-trifluoroethane (HCFC-133b);
tetrafluoroethane, namely, in particular 1,1,2,2-tetrafluoroethane (HFC-134) and 1,1,1,2-tetrafluoroethane (HFC-134a);
chlorodifluoroethane, namely, in particular 1-chloro-2,2-difluoroethane (HCFC-142), 1-chloro-1,2-difluoroethane (HCFC-142a) and 1-chloro-1,1-difluoroethane (HCFC-142b);
trifluoroethane, namely, in particular 1,1,2-trifluoroethane (HFC-143) and 1,1,1-trifluoroethane (HFC-143a);
difluoroethane, namely, in particular 1,1-difluoroethane (HFC-152a) and 1,2-difluoroethane (HFC-152);
difluoroethylene, namely 1,2-difluoroethylene (HFO-1132) and 1,1-difluoroethylene (HFO-1132a); and
fluoroethylene (HFO-1141).

According to a particular embodiment, the (hydro)halocarbon compounds that may be used in the context of the invention comprise 3 carbon atoms.

They may be chosen especially from:
dichlorohexafluoropropane, namely, in particular 1,2-dichloro-1,1,2,3,3,3-hexafluoropropane (HCFC-216ba), 1,3-dichloro-1,1,2,2,3,3-hexafluoropropane (HCFC-216ca), 1,1-dichloro-1,2,2,3,3,3-hexafluoropropane (HCFC-216cb) and 2,2-dichloro-1,1,1,3,3,3-hexafluoropropane (HCFC-216aa);
chloroheptafluoropropane, namely, in particular 1-chloro-1,1,2,2,3,3,3-heptafluoropropane (HCFC-217ca) and 2-chloro-1,1,1,2,3,3,3-heptafluoropropane (HCFC-217ba);
octafluoropropane (HFC-218);
dichloropentafluoropropane, namely, in particular 2,2-dichloro-1,1,1,3,3-pentafluoropropane (HCFC-225aa), 2,3-dichloro-1,1,1,2,3-pentafluoropropane (HCFC-225ba), 1,2-dichloro-1,1,2,3,3-pentafluoropropane (HCFC-225bb), 3,3-dichloro-1,1,1,2,2-pentafluoropropane (HCFC-225ca), 1,3-dichloro-1,1,2,2,3-pentafluoropropane (HCFC-225cb), 1,1-dichloro-1,2,2,3,3-pentafluoropropane (HCFC-225cc), 1,2-dichloro-1,1,3,3,3-pentafluoropropane (HCFC-225da), 1,3-dichloro-1,1,2,3,3-pentafluoropropane (HCFC-225ea) and 1,1-dichloro-1,2,3,3,3-pentafluoropropane (HCFC-225eb);
chlorohexafluoropropane, namely, in particular 2-chloro-1,1,1,2,3,3-hexafluoropropane (HCFC-226ba), 3-chloro-1,1,1,2,2,3-hexafluoropropane (HCFC-226ca), 1-chloro-1,1,2,2,3,3-hexafluoropropane (HCFC-226cb), 2-chloro-1,1,1,3,3,3-hexafluoropropane (HCFC-226da) and 1-chloro-1,1,2,3,3,3-hexafluoropropane (HCFC-226ea);
heptafluoropropane, namely, in particular 1,1,2,2,3,3,3-heptafluoropropane (HFC-227ca) and 1,1,1,2,3,3,3-heptafluoropropane (HFC-227ea);
dichlorotetrafluoropropane, namely, in particular 2,2-dichloro-1,1,3,3-tetrafluoropropane (HCFC-234aa), 2,2-dichloro-1,1,1,3-tetrafluoropropane (HCFC-234ab), 1,2-dichloro-1,2,3,3-tetrafluoropropane (HCFC-234ba), 2,3-dichloro-1,1,1,2-tetrafluoropropane (HCFC-234bb), 1,2-dichloro-1,1,2,3-tetrafluoropropane (HCFC-234bc), 1,3-dichloro-1,2,2,3-tetrafluoropropane (HCFC-234ca), 1,1-dichloro-2,2,3,3-tetrafluoropropane (HCFC-234cb), 1,3-dichloro-1,1,2,2-tetrafluoropropane (HCFC-234cc), 1,1-dichloro-1,2,2,3-tetrafluoropropane (HCFC-234cd), 2,3-dichloro-1,1,1,3-tetrafluoropropane (HCFC-234da), 1,3-dichloro-1,1,3,3-tetrafluoropropane (HCFC-234fa), 1,1-dichloro-1,3,3,3-tetrafluoropropane (HCFC-234fb), 1,1-dichloro-2,3,3,3-tetrafluoropropane (HCFC-234ea), 1,3-dichloro-1,1,2,3-tetrafluoropropane (HCFC-234eb) 1,1-dichloro-1,2,3,3-tetrafluoropropane (HCFC-234ec) and 1,2 dichloro-1,1,3,3-tetrafluoropentane (HCFC-234db);
chloropentafluoropropane, namely, in particular 1-chloro-1,2,2,3,3-pentafluoropropane (HCFC-235ca), 3-chloro-1,1,1,2,3-pentafluoropropane (HCFC-235ea), 1-chloro-1,1,2,2,3-pentafluoropropane (HCFC-235cc), 2-chloro-1,1,1,3,3-pentafluoropropane (HCFC-235da), 1-chloro-1,1,3,3,3-pentafluoropropane (HCFC-235fa), 1-chloro-1,1,2,3,3-pentafluoropropane (HCFC-235eb), 3-chloro-1,1,1,2,2-pentafluoropropane (HCFC-235cb), 2-chloro-1,1,2,3,3-pentafluoropropane (HCFC-235ba) and 2-chloro-1,1,1,2,3-pentafluoropropane (HCFC-235bb);

hexafluoropropane, namely, in particular 1,1,1,2,2,3-hexafluoropropane (HFC-236cb), 1,1,1,2,3,3-hexafluoropropane (HFC-236ea), 1,1,1,3,3,3-hexafluoropropane (HFC-236fa) and 1,1,2,2,3,3-hexafluoropropane (HFC-236ca);

tetrachlorofluoropropane, namely, in particular 1,1,3,3-tetrachloro-1-fluoropropane (HCFC-241fa), 1,1,1,3-tetrachloro-3-fluoropropane (HCFC-241fb), 1,1,3,3-tetrachloro-2-fluoropropane (HCFC-241ea), 1,1,1,3-tetrachloro-2-fluoropropane (HCFC-241eb), 1,1,2,3-tetrachloro-3-fluoropropane (HCFC-241da), 1,1,2,3-tetrachloro-1-fluoropropane (HCFC-241db), 1,1,1,2-tetrachloro-3-fluoropropane (HCFC-241dc), 1,1,2,3-tetrachloro-2-fluoropropane (HCFC-241ba), 1,1,1,2-tetrachloro-2-fluoropropane (HCFC-241bb), 1,2,2,3-tetrachloro-1-fluoropropane (HCFC-241aa), 1,1,2,2-tetrachloro-3-fluoropropane (HCFC-241ab) and 1,1,2,2-tetrachloro-1-fluoropropane (HCFC-241ac);

trichlorodifluoropropane, namely, in particular 1,3,3-trichloro-1,1-difluoropropane (HCFC-242fa), 1,1,3-trichloro-1,3-difluoropropane (HCFC-242fb), 1,1,1-trichloro-3,3-difluoropropane (HCFC-242fc), 1,1,3-trichloro-2,3-difluoropropane (HCFC-242ea), 1,1,3-trichloro-1,2-difluoropropane (HCFC-242eb), 1,1,1-trichloro-2,3-difluoropropane (HCFC-242ec), 1,2,3-trichloro-1,3-difluoropropane (HCFC-242da), 1,1,2-trichloro-3,3-difluoropropane (HCFC-242db), 1,2,3-trichloro-1,1-difluoropropane (HCFC-242dc), 1,1,2-dichloro-1,3-difluoropropane (HCFC-242dd), 1,1,3-trichloro-2,2-difluoropropane (HCFC-242ca), 1,1,1-trichloro-2,2-difluoropropane (HCFC-242cb), 1,2,3-trichloro-1,2-difluoropropane (HCFC-242ba), 1,1,2-trichloro-2,3-difluoropropane (HCFC-242bb), 1,1,2-trichloro-1,2-difluoropropane (HCFC-242bc), 2,2,3-trichloro-1,1-difluoropropane (HCFC-242aa), 1,2,2-trichloro-1,3-difluoropropane (HCFC-242ab) and 1,2,2-trichloro-1,1-difluoropropane (HCFC-242ac);

dichlorotrifluoropropane, namely, in particular 1,1-dichloro-3,3,3-trifluoropropane (HCFC-243fa), 1,3-dichloro-1,1,3-trifluoropropane (HCFC-243fb), 1,1-dichloro-1,3,3-trifluoropropane (HCFC-243fc), 1,3-dichloro-1,2,3-trifluoropropane (HCFC-243ea), 1,1-dichloro-2,3,3-trifluoropropane (HCFC-243eb), 1,3-dichloro-1,1,2-trifluoropropane (HCFC-243ec), 1,1-dichloro-1,2,3-trifluoropropane (HCFC-243ed), 1,2-dichloro-1,3,3-trifluoropropane (HCFC-243da), 2,3-dichloro-1,1,1-trifluoropropane (HCFC-243db), 1,2-dichloro-1,1,3-trifluoropropane (HCFC-243dc), 1,3-dichloro-1,2,2-trifluoropropane (HCFC-243ca), 1,1-dichloro-2,2,3-trifluoropropane (HCFC-243cb), 1,1-dichloro-1,2,2-trifluoropropane (HCFC-243cc), 2,3-dichloro-1,1,2-trifluoropropane (HCFC-243ba), 1,2-dichloro-1,2,3-trifluoropropane (HCFC-243bb), 1,2-dichloro-1,1,2-trifluoropropane (HCFC-243bc), 2,2-dichloro-1,1,3-trifluoropropane (HCFC-243aa) and 2,2-dichloro-3,3,3-trifluoropropane (HCFC-243ab);

chlorotetrafluoropropane, namely, in particular 2-chloro-1,2,3,3-tetrafluoropropane (HCFC-244ba), 2-chloro-1,1,1,2-tetrafluoropropane (HCFC-244bb), 3-chloro-1,1,2,2-tetrafluoropropane (HCFC-244ca), 1-chloro-1,2,2,3-tetrafluoropropane (HCFC-244cb), 1-chloro-1,2,2-tetrafluoropropane (HCFC-244cc), 2-chloro-1,1,3,3-tetrafluoropropane (HCFC-244da), 2-chloro-1,1,1,3-tetrafluoropropane (HCFC-244db), 3-chloro-1,1,2,3-tetrafluoropropane (HCFC-244ea), 3-chloro-1,1,1,2-tetrafluoropropane (HCFC-244eb), 1-chloro-1,1,2,3-tetrafluoropropane (HCFC-244ec), 3-chloro-1,1,1,3-tetrafluoropropane (HCFC-244fa) and 1-chloro-1,1,3,3-tetrafluoropropane (HCFC-244fb);

pentafluoropropane, namely, in particular 1,1,2,2,3-pentafluoropropane (HFC-245ca), 1,1,2,3,3-pentafluoropropane (HFC-245ea), 1,1,1,2,3-pentafluoropropane (HFC-245eb), 1,1,1,2,2-pentafluoropropane (HFC-245cb) and 1,1,1,3,3-pentafluoropropane (HFC-245fa);

chlorotrifluoropropane, namely, in particular 2-chloro-1,2,3-trifluoropropane (HCFC-253ba), 2-chloro-1,1,2-trifluoropropane (HCFC-253bb), 1-chloro-2,2,3-trifluoropropane (HCFC-253ca), 1-chloro-1,2,2-trifluoropropane (HCFC-253cb), 3-chloro-1,1,2-trifluoropropane (HCFC-253ea), 1-chloro-1,2,3-trifluoropropane (HCFC-253eb), 1-chloro-1,1,2-trifluoropropane (HCFC-253ec), 1-chloro-1,3,3-trifluoropropane (HCFC-253fa), 3-chloro-1,1,1-trifluoropropane (HCFC-253fb), 1-chloro-1,1,3-trifluoropropane (HCFC-253fc), 2-chloro-1,1,3-trifluoropropane (HCFC-253da) and 2-chloro-1,1,1-trifluoropropane (HCFC-253db);

tetrafluoropropane, namely, in particular 1,1,2,2-tetrafluoropropane (HFC-254cb), 1,1,1,3-tetrafluoropropane (HFC-254fb), 1,1,2,3-tetrafluoropropane (HFC-254ea), 1,1,1,2-tetrafluoropropane (HFC-254eb), 1,2,2,3-tetrafluoropropane (HFC-254ca) and 1,1,3,3-tetrafluoropropane (HFC-254fa);

chlorodifluoropropane, namely, in particular 1-chloro-2,2-difluoropropane (HCFC-262ca), 3-chloro-1,1-difluoropropane (HCFC-262fa), 1-chloro-1,3-difluoropropane (HCFC-262fb), 1-chloro-1,1-difluoropropane (HCFC-262fc), 1-chloro-2,3-difluoropropane (HCFC-262ea), 1-chloro-1,2-difluoropropane (HCFC-262eb), 2-chloro-1,3-difluoropropane (HCFC-262da), 2-chloro-1,1-difluoropropane (HCFC-262db) and 2-chloro-1,2-difluoropropane (HCFC-262ba);

trifluoropropane (HFC-263), namely, in particular 1,1,1-trifluoropropane (HFC-263fb), 1,1,3-trifluoropropane (HFC-263fa), 1,2,3-trifluoropropane (HFC-263ea), 1,1,2-trifluoropropane (HFC-263eb) and 1,2,2-trifluoropropane (HFC-263ca);

dichlorotetrafluoropropene (HCFO-1214), namely, in particular 1,2-dichloro-1,3,3,3-tetrafluoropropene (HCFO-1214xb), 1,1-dichloro-2,3,3,3-tetrafluoropropene (HCFO-1214ya), 1,3-dichloro-1,2,3,3-tetrafluoropropene (HCFO-1214yb), 2,3-dichloro-1,1,3,3-tetrafluoropropene (HCFO-1214xc) and 3,3-dichloro-1,1,2,3-tetrafluoropropene (HCFO-1214yc);

chloropentafluoropropene (HCFO-1215), namely, in particular 1-chloropentafluoropropene, 2-chloropentafluoropropene and 3-chloropentafluoropropene;

hexafluoropropene (HFO-1216);

dichlorotrifluoropropene (HCFO-1223), namely, in particular 1,1-dichloro-3,3,3-trifluoropropene (HCFO-1223za), 1,2-dichloro-3,3,3-trifluoropropene (HCFO-1223xd), 2,3-dichloro-1,3,3-trifluoropropene (HCFO-1223xe), 1,3-dichloro-2,3,3-trifluoropropene (HCFO-1223yd), 1,2-dichloro-1,3,3-trifluoropropene (HCFO-1223xb), 2,3-dichloro-1,1,3-trifluoropropene (HCFO-1223xc), 1,1-dichloro-2,3,3-trifluoropropene (HCFO-1223ya), 1,3-dichloro-2,2,3-trifluoropropene (HCFO-1223yb), 3,3-dichloro-1,1,2-trifluoropropene (HCFO-1223yc), 3,3-dichloro-1,2,3-trifluoropropene (HCFO- 1223ye), 1,3-dichloro-1,3,3-trifluoropropene (HCFO-1223zb) and 3,3-dichloro-1,1,3-trifluoropropene (HCFO-1223zc);

chlorotetrafluoropropene (HCFO-1224), namely, in particular 1-chloro-2,3,3,3-tetrafluoropropene (HCFO-1224yd), 1-chloro-1,3,3,3-tetrafluoropropene (HCFO-1224zb), 2-chloro-1,3,3,3-tetrafluoropropene (HCFO-1224xe), 3-chloro-1,2,3,3-tetrafluoropropene (HCFO-1224ye), 3-chloro-1,1,3,3-tetrafluoropropene (HCFO-1224zc), 2-chloro-1,1,3,3-tetrafluoropropene (HCFO-1224xc), 1-chloro-1,2,3,3-tetrafluoropropene (HCFO-1224yb) and 3-chloro-1,1,2,3-tetrafluoropropene (HCFO-1224yc);

pentafluoropropene, namely, in particular 1,1,1,2,3-pentafluoropropene in trans form (HFO-1225yeE), 1,1,1,2,3-pentafluoropropene in cis form (HFO-1225yeZ), 1,1,3,3,3-pentafluoropropene (HFO-1225zc) and 1,1,2,3,3-pentafluoropropene (HFO-1225yc);

trichlorofluoropropene (HCFO-1231), namely, in particular 1,1,2-trichloro-3-fluoropropene (HCFO-1231xa), 1,2,3-trichloro-1-fluoropropene (HCFO-1231xb), 1,2,3-trichloro-3-fluoropropene (HCFO-1231xd), 2,3,3-trichloro-1-fluoropropene (HCFO-1231xe), 2,3,3-trichloro-3-fluoropropene (HCFO-1231xf), 1,1,3-trichloro-2-fluoropropene (HCFO-1231ya), 1,3,3-trichloro-2-fluoropropene (HCFO-1231yd), 3,3,3-trichloro-2-fluoropropene (HCFO-1231yf), 1,1,3-trichloro-3-fluoropropene (HCFO-1231za), 1,3,3-trichloro-1-fluoropropene (HFCO-1231zb), 1,3,3-trichloro-3-fluoropropene (HCFO-1231zd) and 3,3,3-trichloro-1-fluoropropene (HCFO-1231ze);

dichlorodifluoropropene (HCFO-1232), namely, in particular 2,3-dichloro-3,3-difluoropropene (HCFO-1232xf), 1,2-dichloro-1,3-difluoropropene (HCFO-1232xb), 2,3-dichloro-1,1-difluoropropene (HCFO-1232xc), 1,2-dichloro-3,3-difluoropropene (HCFO-1232xd), 2,3-dichloro-1,3-difluoropropene (HCFO-1232xe), 1,1-dichloro-2,3-difluoropropene (HCFO-1232ya), 1,3-dichloro-1,2-difluoropropene (HCFO-1232yb), 1,3-dichloro-2,3-difluoropropene (HCFO-1232yd), 3,3-dichloro-1,2-difluoropropene (HCFO-1232ye), 3,3-dichloro-2,3-difluoropropene (HCFO-1232yf), 1,1-dichloro-3,3-difluoropropene (HCFO-1232za), 1,3-dichloro-1,3-difluoropropene (HCFO-1232zb), 3,3-dichloro-1,1-difluoropropene (HCFO-1232zc), 1,3-dichloro-3,3-difluoropropene (HCFO-1232zd) and 3,3-dichloro-1,3-difluoropropene (HCFO-1232ze);

chlorotrifluoropropene, namely, in particular 2-chloro-1,1,3-trifluoropropene (HCFO-1233xc), 2-chloro-1,3,3-trifluoropropene (HCFO-1233xe), 1-chloro-1,2,3-trifluoropropene (HCFO-1233yb), 3-chloro-1,1,2-trifluoropropene (HCFO-1233yc), 1-chloro-2,3,3-trifluoropropene (HCFO-1233yd), 3-chloro-1,2,3-trifluoropropene (HCFO-1233ye), 3-chloro-2,3,3-trifluoropropene (HCFO-1233yf), 1-chloro-1,3,3-trifluoropropene (HCFO-1233zb), 3-chloro-1,1,3-trifluoropropene (HCFO-1233zc), 3-chloro-1,3,3-trifluoropropene (HCFO-1233ze), 2-chloro-3,3,3-trifluoro-propene (HCFO-1233xf) and 1-chloro-3,3,3-trifluoropropene in trans form (HCFO-1233zdE);

tetrafluoropropene, namely, in particular 1,1,2,3-tetrafluoropropene (HFO-1234yc), 2,3,3,3-tetrafluoropropene (HFO-1234yf), 1,2,3,3-tetrafluoropropene (HFO-1234ye), 1,1,3,3-tetrafluoropropene (HFO-1234zc), 1,3,3,3-tetrafluoropropene in cis form (HFO-1234zeZ) and 1,3,3,3-tetrafluoropropene in trans form (HFO-1234zeE);

chlorodifluoropropene (HCFO-1242), namely, in particular 3-chloro-3,3-difluoropropene (HCFO-1242zf), 3-chloro-1,3-difluoropropene (HCFO-1242ze), 2-chloro-1,1-difluoropropene (HCFO-1242xc), 2-chloro-1,3-difluoropropene (HCFO-1242xe), 2-chloro-3,3-difluoropropene (HCFO-1242xf), 1-chloro-1,2-difluoropropene (HCFO-1242yb), 1-chloro-2,3-difluoropropene (HCFO-1242yd), 3-chloro-1,2-difluoropropene (HCFO-1242ye), 3-chloro-2,3-difluoropropene (HCFO-1242yf), 1-chloro-1,3-difluoropropene (HCFO-1242zb), 3-chloro-1,1-difluoropropene (HCFO-1242zc) and 1-chloro-3,3-difluoropropene (HCFO-1242zd);

trifluoropropene, namely, in particular 1,1,2-trifluoropropene (HFO-1243yc), 1,2,3-trifluoropropene (HFO-1243ye), 2,3,3-trifluoropropene (HFO-1243yf), 1,1,3-trifluoropropene (HFO-1243zc), 1,3,3-trifluoropropene (HFO-1243ze) and 3,3,3-trifluoropropene (HFO-1243zf);

chlorofluoropropene (HCFO-1251), namely, in particular 1-chloro-3-fluoropropene (HCFO-1251zd), 1-chloro-1-fluoropropene (HCFO-1251zb), 1-chloro-2-fluoropropene (HCFO-1251yd), 2-chloro-1-fluoropropene (HCFO-1251xe), 2-chloro-3-fluoropropene (HCFO-1251yf), 3-chloro-2-fluoropropene (HCFO-1251xf), 3-chloro-1-fluoropropene (HCFO-1251ze and 3-chloro-3-fluoropropene (HCFO-1251zf);

difluoropropene (HFO-1252), namely, in particular 1,2-difluoropropene (HCFO-1252ye), 2,3-difluoropropene (HCFO-1252yf), 1,1-difluoropropene (HCFO-1252zc), 1,3-difluoropropene (HCFO-1252ze) and 3,3-difluoropropene (HCFO-1252zf); and trifluoropropyne.

The compositions according to the invention may be ternary mixtures, i.e. mixtures of three compounds and only three.

The compositions according to the invention may be quaternary mixtures, i.e. mixtures of four compounds and only four.

The compositions according to the invention may be quinternary mixtures, i.e. mixtures of five compounds and only five.

The compositions according to the invention may be senary mixtures, i.e. mixtures of six compounds and only six.

The compositions according to the invention may also be mixtures of seven compounds and only seven.

The compositions according to the invention may also be mixtures of eight compounds and only eight.

The compositions according to the invention may also be mixtures comprising more than eight compounds.

According to one embodiment, the compositions according to the invention consist essentially of a mixture of HF, HCFO-1233zdZ and one or more (hydro)halocarbon compounds comprising from 1 to 3 carbon atoms—the maximum amount of impurities, other than these compounds, being, for example, 2%, or 1%, or 0.5%, or 0.2%, or 0.1%, or 0.05%, or 0.02%, or 0.01%.

According to one embodiment, the compositions of the invention consist of a mixture of HF, HCFO-1233zdZ and one or more (hydro)halocarbon compounds comprising from 1 to 3 carbon atoms.

According to one embodiment, the abovementioned (hydro)halocarbon compound(s) used in the compositions according to the invention are chosen from tetrachlorofluoropropanes, trichlorodifluoropropanes, dichlorotrifluoropropanes, chlorotetrafluoropropanes, pentafluoropropanes, dichlorodifluoropropenes, trichlorofluoropropenes, chlorotrifluoropropenes and tetrafluoropropenes, and mixtures thereof.

According to one embodiment, the abovementioned (hydro)halocarbon compound(s) used in the compositions according to the invention are chosen from HCFC-241fa, HCFC-242fa, HCFC-243fa, HCFC-244fa, HFC-245fa, HCFO-1232za, HCFO-1232zd, HCFO-1233zdE, HFO-1234zeZ and HFO-1234zeE.

According to one embodiment, the abovementioned (hydro)halocarbon compound(s) used in the compositions according to the invention are chosen from HFC-245fa, HCFO-1233zdE, HFO-1234zeZ and HFO-1234zeE.

According to one embodiment, the compositions according to the invention may consist (or consist essentially) of a mixture of HF, HCFO-1233zdE and HCFO-1233zdZ. The HF content in these compositions is advantageously from 1% to 85% and more preferentially from 5% to 80%. The boiling point is preferably from 0 to 40° C. for a pressure from 0.6 to 4.0 bar absolute.

Alternatively, the compositions according to the invention may comprise a mixture of HF, HCFO-1233zdE, HCFO-1233zdZ and of one or more other (hydro)halocarbon compounds, which may be chosen from all the compounds listed above; and which may be chosen especially from propanes and propenes, which are partially or totally substituted with halogens; and which may be chosen especially from tetrachlorofluoropropanes, trichlorodifluoropropanes, dichlorotrifluoropropanes, chlorotetrafluoropropanes, pentafluoropropanes, dichlorodifluoropropenes, trichlorofluoropropenes, chlorotrifluoropropenes and tetrafluoropropenes; and which may be chosen especially from HCFC-241fa, HCFC-242fa, HCFC-243fa, HCFC-244fa, HFC-245fa, HCFO-1232za, HCFO-1232zd, HFO-1234zeZ and HFO-1234zeE; and which may be chosen more particularly from HFC-245fa, HFO-1234zeZ and HFO-1234zeE.

According to one embodiment, the compositions according to the invention may consist (or consist essentially) of a mixture of HF, HCFO-1233zdE, HCFO-1233zdZ and HFC-245fa. The HF content in these compositions is advantageously from 1% to 85% and more preferentially from 5% to 80%. The boiling point is preferably from 0 to 40° C. for a pressure from 0.6 to 4.4 bar absolute.

Alternatively, the compositions according to the invention may comprise a mixture of HF, HCFO-1233zdE, HCFO-1233zdZ, HFC-245fa and of one or more other (hydro)halocarbon compounds, which may be chosen from all the compounds listed above; and which may be chosen especially from propanes and propenes, which are partially or totally substituted with halogens; and which may be chosen especially from tetrachlorofluoropropanes, trichlorodifluoropropanes, dichlorotrifluoropropanes, chlorotetrafluoropropanes, pentafluoropropanes, dichlorodifluoropropenes, trichlorofluoropropenes, chlorotrifluoropropenes and tetrafluoropropenes; and which may be chosen especially from HCFC-241fa, HCFC-242fa, HCFC-243fa, HCFC-244fa, HCFO-1232za, HCFO-1232zd, HFO-1234zeZ and HFO-1234zeE; and which may be chosen more particularly from HFO-1234zeZ and HFO-1234zeE.

According to one embodiment, the compositions according to the invention may consist (or consist essentially) of a mixture of HF, HCFO-1233zdZ, HFO-1234zeZ and HFC-245fa. The HF content in these compositions is advantageously from 1% to 85% and more preferentially from 5% to 80%. The boiling point is preferably from 0 to 40° C. for a pressure from 0.6 to 4.8 bar absolute.

Alternatively, the compositions according to the invention may comprise a mixture of HF, HCFO-1233zdZ, HFO-1234zeZ, HFC-245fa and of one or more other (hydro)halocarbon compounds, which may be chosen from all the compounds listed above; and which may be chosen especially from propanes and propenes, which are partially or totally substituted with halogens; and which may be chosen especially from tetrachlorofluoropropanes, trichlorodifluoropropanes, dichlorotrifluoropropanes, chlorotetrafluoropropanes, pentafluoropropanes, dichlorodifluoropropenes, trichlorofluoropropenes, chlorotrifluoropropenes and tetrafluoropropenes; and which may be chosen especially from HCFC-241fa, HCFC-242fa, HCFC-243fa, HCFC-244fa, HCFO-1232za, HCFO-1232zd, HCFO-1233zdE and HFO-1234zeE; and which may be chosen more particularly from HCFO-1233zdE and HFO-1234zeE.

According to one embodiment, the compositions according to the invention may consist (or consist essentially) of a mixture of HF, HCFO-1233zdZ, HFO-1234zeE and HFC-245fa. The HF content in these compositions is advantageously from 1% to 80% and more preferentially from 5% to 75%. The boiling point is preferably from 0 to 40° C. for a pressure from 0.6 to 8.6 bar absolute.

Alternatively, the compositions according to the invention may comprise a mixture of HF, HCFO-1233zdZ, HFO-1234zeE, HFC-245fa and of one or more other (hydro)halocarbon compounds, which may be chosen from all the compounds listed above; and which may be chosen especially from propanes and propenes, which are partially or totally substituted with halogens; and which may be chosen especially from tetrachlorofluoropropanes, trichlorodifluoropropanes, dichlorotrifluoropropanes, chlorotetrafluoropropanes, pentafluoropropanes, dichlorodifluoropropenes, trichlorofluoropropenes, chlorotrifluoropropenes and tetrafluoropropenes; and which may be chosen especially from HCFC-241fa, HCFC-242fa, HCFC-243fa, HCFC-244fa, HCFO-1232za, HCFO-1232zd, HCFO-1233zdE and HFO-1234zeZ; and which may be chosen more particularly from HCFO-1233zdE and HFO-1234zeZ.

According to one embodiment, the compositions according to the invention may consist (or consist essentially) of a mixture of HF, HCFO-1233zdZ, HFO-1234zeE, HFO-1234zeZ and HFC-245fa. The HF content in these compositions is advantageously from 1% to 85% and more preferentially from 5% to 80%. The boiling point is preferably from 0 to 40° C. for a pressure from 0.6 to 8.9 bar absolute.

Alternatively, the compositions according to the invention may comprise a mixture of HF, HCFO-1233zdZ, HFO-1234zeE, HFO-1234zeZ, HFC-245fa and of one or more other (hydro)halocarbon compounds, which may be chosen from all the compounds listed above; and which may be chosen especially from propanes and propenes, which are partially or totally substituted with halogens; and which may be chosen especially from tetrachlorofluoropropanes, trichlorodifluoropropanes, dichlorotrifluoropropanes, chlorotetrafluoropropanes, pentafluoropropanes, dichlorodifluoropropenes, trichlorofluoropropenes, chlorotrifluoropropenes and tetrafluoropropenes; and which may be chosen especially from HCFC-241fa, HCFC-242fa, HCFC-243fa, HCFC-244fa, HCFO-1232za, HCFO-1232zd and HCFO-1233zdE; and which may especially be HCFO-1233zdE.

According to one embodiment, the compositions according to the invention may consist (or consist essentially) of a mixture of HF, HCFO-1233zdZ, HCFO-1233zdE, HFO-1234zeE and HFC-245fa. The HF content in these compositions is advantageously from 1% to 85% and more preferentially from 5% to 80%. The boiling point is preferably from 0 to 40° C. for a pressure from 0.6 to 8.9 bar absolute.

Alternatively, the compositions according to the invention may comprise a mixture of HF, HCFO-1233zdZ, HCFO-1233zdE, HFO-1234zeE, HFC-245fa and of one or more other (hydro)halocarbon compounds, which may be chosen from all the compounds listed above; and which may be chosen especially from propanes and propenes, which are partially or totally substituted with halogens; and which may be chosen especially from tetrachlorofluoropropanes, trichlorodifluoropropanes, dichlorotrifluoropropanes, chlorotetrafluoropropanes, pentafluoropropanes, dichlorodifluoropropenes, trichlorofluoropropenes, chlorotrifluoropropenes and tetrafluoropropenes; and which may be chosen especially from HCFC-241fa, HCFC-242fa, HCFC-243fa, HCFC-244fa, HCFO-1232za, HCFO-1232zd and HFO-1234zeZ; and which may especially be HFO-1234zeZ.

According to one embodiment, the compositions according to the invention may consist (or consist essentially) of a mixture of HF, HCFO-1233zdZ, HCFO-1233zdE, HFO-1234zeZ and HFC-245fa. The HF content in these compositions is advantageously from 1% to 85% and more preferentially from 5% to 80%. The boiling point is preferably from 0 to 40° C. for a pressure from 0.6 to 4.8 bar absolute.

Alternatively, the compositions according to the invention may comprise a mixture of HF, HCFO-1233zdZ, HCFO-1233zdE, HFO-1234zeZ, HFC-245fa and of one or more other (hydro)halocarbon compounds, which may be chosen from all the compounds listed above; and which may be chosen especially from propanes and propenes, which are partially or totally substituted with halogens; and which may be chosen especially from tetrachlorofluoropropanes, trichlorodifluoropropanes, dichlorotrifluoropropanes, chlorotetrafluoropropanes, pentafluoropropanes, dichlorodifluoropropenes, trichlorofluoropropenes, chlorotrifluoropropenes and tetrafluoropropenes; and which may be chosen especially from HCFC-241fa, HCFC-242fa, HCFC-243fa, HCFC-244fa, HCFO-1232za, HCFO-1232zd and HFO-1234zeE; and which may especially be HFO-1234zeE.

According to one embodiment, the compositions according to the invention may consist (or consist essentially) of a mixture of HF, HCFO-1233zdZ, HCFO-1233zdE, HFO-1234zeE, HFO-1234zeZ and HFC-245fa. The HF content in these compositions is advantageously from 1% to 85% and more preferentially from 5% to 80%. The boiling point is preferably from 0 to 40° C. for a pressure from 0.6 to 8.8 bar absolute.

Alternatively, the compositions according to the invention may comprise a mixture of HF, HCFO-1233zdZ, HCFO-1233zdE, HFO-1234zeE, HFO-1234zeZ, HFC-245fa and of one or more other (hydro)halocarbon compounds, which may be chosen from all the compounds listed above; and which may be chosen especially from propanes and propenes, which are partially or totally substituted with halogens; and which may be chosen especially from tetrachlorofluoropropanes, trichlorodifluoropropanes, dichlorotrifluoropropanes, chlorotetrafluoropropanes, pentafluoropropanes, dichlorodifluoropropenes, trichlorofluoropropenes, chlorotrifluoropropenes and tetrafluoropropenes; and which may be chosen especially from HCFC 241fa, HCFC-242fa, HCFC-243fa, HCFC-244fa, HFO 1232za and HCFO-1232zd.

In general, in the compositions according to the invention, the proportion of HF is preferably from 1% to 85%, especially from 5% to 80% (relative to the total weight of the composition), more particularly from 10% to 65%; and the proportion of (hydro)halocarbon compounds, including HCFO-1233zdZ, is from 15% to 99%, especially from 20% to 95%, more particularly from 35% to 90%.

The boiling point of a composition according to the invention is preferably from −20° C. to 80° C. for a pressure from 0.1 to 44 bar absolute; advantageously from 0 to 40° C. for a pressure from 0.5 to 9 bar absolute.

When the compositions according to the invention comprise both HCFO-1233zdZ and HCFO-1233zdE, they may comprise, in mass proportions relative to the sum of these two compounds:
- from 1% to 10% of HCFO-1233zdZ and from 90% to 99% of HCFO-1233zdE;
- from 10% to 20% of HCFO-1233zdZ and from 80% to 90% of HCFO-1233zdE;
- from 20% to 30% of HCFO-1233zdZ and from 70% to 80% of HCFO-1233zdE;
- from 30% to 40% of HCFO-1233zdZ and from 60% to 70% of HCFO-1233zdE;
- from 40% to 50% of HCFO-1233zdZ and from 50% to 60% of HCFO-1233zdE;
- from 50% to 60% of HCFO-1233zdZ and from 40% to 50% of HCFO-1233zdE;
- from 60% to 70% of HCFO-1233zdZ and from 30% to 40% of HCFO-1233zdE;
- from 70% to 80% of HCFO-1233zdZ and from 20% to 30% of HCFO-1233zdE;
- from 80% to 90% of HCFO-1233zdZ and from 10% to 20% of HCFO-1233zdE;
- from 90% to 99% of HCFO-1233zdZ and from 1% to 10% of HCFO-1233zdE.

According to one embodiment, the compositions according to the invention, in condensed form, comprise two liquid phases, one preferably being richer in HF than the other.

The invention may in particular be exploited in the context of processes for producing a fluoro compound, in which mixtures of the compounds described above may be produced.

Such mixtures may then be treated by distillation so as to collect, firstly, a composition according to the invention, and, secondly, HF, or alternatively, thirdly, HCFO-1233zdZ, or alternatively, fourthly, one or more other (hydro)halocarbon compounds.

Such mixtures may especially be obtained as a stream of products derived from a reaction for the catalytic fluorination of a chloro compound to a fluoro compound with HF.

The term "chloro compound" (which represents the main reagent of the catalytic fluorination reaction) means an organic compound comprising one or more chlorine atoms, and the term "fluoro compound" (which represents the desired product of the catalytic fluorination reaction) means an organic compound comprising one or more fluorine atoms.

It is understood that the chloro compound may comprise one or more fluorine atoms, and that the fluoro compound may comprise one or more chlorine atoms. In general, the number of chlorine atoms in the fluoro compound is less than the number of chlorine atoms in the chloro compound; and the number of fluorine atoms in the fluoro compound is greater than the number of fluorine atoms in the chloro compound.

The chloro compound may be an alkane or an alkene optionally bearing substituents chosen from F, Cl, I and Br (preferably from F and Cl), and comprising at least one Cl substituent.

The fluoro compound may be an alkane or an alkene optionally bearing substituents chosen from F, Cl, I and Br (preferably from F and Cl), and comprising at least one F substituent.

The chloro compound may especially be an alkane with one or more chlorine substituents (hydrochlorocarbon or chlorocarbon) or an alkane with one or more chlorine and fluorine substituents (hydrochlorofluorocarbon or chlorofluorocarbon) or an alkene with one or more chlorine substituents (chloroolefin or hydrochloroolefin) or an alkene with one or more chlorine and fluorine substituents (hydrochlorofluoroolefin or chlorofluoroolefin).

The fluoro compound may especially be an alkane with one or more fluorine substituents (fluorocarbon or hydrofluorocarbon) or an alkane with one or more chlorine and fluorine substituents (hydrochlorofluorocarbon or chlorofluorocarbon) or an alkene with one or more fluorine substituents (fluoroolefin or hydrofluoroolefin) or an alkene with one or more chlorine and fluorine substituents (hydrochlorofluoroolefin or chlorofluoroolefin).

According to one embodiment, the chloro compound and the fluoro compound comprise only one carbon atom.

According to one embodiment, the chloro compound and the fluoro compound comprise two carbon atoms.

According to a particularly preferred embodiment, the chloro compound and the fluoro compound comprise three carbon atoms.

The invention is especially found to apply to the following fluorination reactions:
  fluorination of 1,1,1,3,3-pentachloropropane to HCFO-1233zdE;
  fluorination of 1,1,3,3-tetrachloropropene to HCFO-1233zdE.

The invention may especially apply to the determination of the decantation and purification steps necessary for treating a gas stream exiting a liquid-phase fluorination reactor using 1,1,3,3-tetrachloropropene as starting material or a gas-phase fluorination reactor using 1,1,1,3,3-pentachloropropane as starting material. This gas stream may contain between 15% and 50% of HF, between 15% and 50% of HCl and the remainder is constituted of all of the organic compounds derived from the reaction.

In one embodiment, a liquid-phase fluorination process is performed using 1,1,3,3-tetrachloropropene as starting material, and the distribution of the organic compounds on conclusion of the reaction may especially be the following: from 85% to 95% of HCFO-1233zdE, from 0 to 5% of HCFO-1233zdZ, from 0 to 3% of HFO-1234zeE, from 0 to 3% of HFO-1234zeZ, from 0 to 3% of HFC-245fa, from 0 to 3% of HCFO-1232, from 0 to 1% of HCFC-243 and from 0 to 1% of HCFC-241.

In one embodiment, a gas-phase fluorination process is performed using 1,1,1,3,3-pentachloropropane as starting material, and the distribution of the organic compounds on conclusion of the reaction may especially be the following: from 65% to 85% of HCFO-1233zdE, from 15% to 25% of HCFO-1233zdZ, from 0 to 10% of HCFO-1232, from 0 to 3% of HFO-1234zeE, from 0 to 3% of HFO-1234zeZ, from 0 to 3% of HFC-245fa, from 0 to 3% of HCFC-243.

The compositions according to the invention have advantageous properties, in particular for the recycling of HF into the reaction step. Thus, the condensed phase of these compositions, optionally when they are subjected to a distillation step and/or a liquid/liquid separation step, such as by decantation, forms two immiscible liquid phases. The phase that is richer in HF may be recycled into the reaction step, whereas the phase that is less rich in HF may be subjected to one or more distillation steps to separate the organic compounds and to allow, for example, recycling into the reaction step of organic compounds that are reaction intermediates.

EXAMPLES

The examples that follow illustrate the invention without limiting it.

Example 1—HF/HCFO-1233zdE/HCFO-1233zdZ Ternary Composition

Azeotropic and hetero-azeotropic behavior was observed for the HF/HCFO-1233zdE/HCFO-1233zdZ ternary mixture.

FIG. 1 illustrates the azeotropic behavior for the isotherm at 25° C., for various HCFO-1233zdE/HCFO-1233zdZ proportions, namely:
  A: 95% HCFO-1233zdE and 5% HCFO-1233zdZ (relative to the total for the two);
  B: 50% HCFO-1233zdE and 50% HCFO-1233zdZ (relative to the total for the two);
  C: 5% HCFO-1233zdE and 95% HCFO-1233zdZ (relative to the total for the two).

It is found that the composition has a boiling point of 0 to 40° C. for a pressure from 0.6 bar absolute to 4.0 bar absolute approximately. Thus, for a mixture of HF with 50% HCFO-1233zdZ and 50% HCFO-1233zdE (the proportions being relative to the sum for the two), the boiling point is 0° C. at about 0.9 bar absolute, 25° C. at about 2.1 bar absolute and 40° C. at about 3.5 bar absolute.

The decantation ranges for a mixture of HF with 50% HCFO-1233zdZ and 50% HCFO-1233zdE (the proportions being relative to the sum for the two) are: from 5% to 75% HF at 0° C.; from 5% to 70% HF at 25° C.; and from 5% to 60% HF at 40° C.

Example 2—HF/HCFO-1233zdZ/HFO-1234zeE/HFC-245fa Quaternary Composition

Azeotropic and hetero-azeotropic behavior was observed for the HF/HCFO-1233zdZ/HFO-1234zeE/HFC-245fa quaternary mixture.

Figure 2:
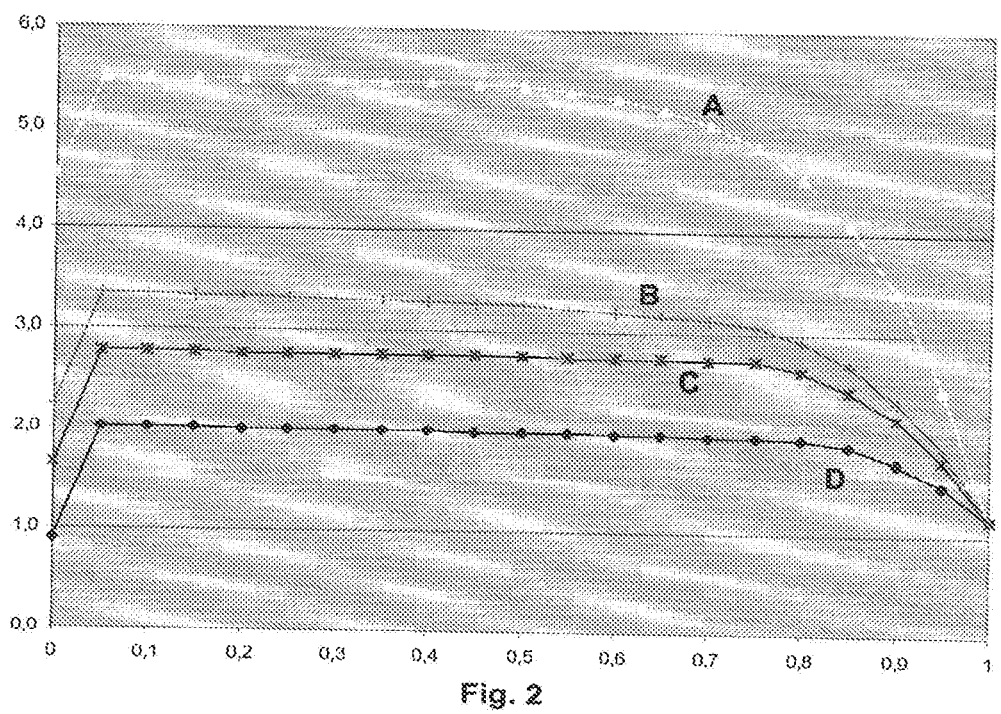
FIG. 2 represents the vapor pressure (on the y-axis, in bar absolute) of mixtures according to the invention in accordance with Example 2, for the 25° C. isotherm. The mass fraction of HF in the composition is given on the x-axis. Curves A, B, C and D correspond to various compositions of (hydro)halocarbon compounds (see Example 2).

FIG. 2 illustrates the azeotropic behavior for the isotherm at 25° C., for various HCFO-1233zdZ/HFO-1234zeE/HFC-245fa proportions, namely:
  A: 5% HCFO-1233zdZ, 90% HFO-1234zeE and 5% HFC-245fa (relative to the total for the three);
  B: 40% HCFO-1233zdZ, 30% HFO-1234zeE and 30% HFC-245fa (relative to the total for the three);
  C: 5% HCFO-1233zdZ, 5% HFO-1234zeE and 90% HFC-245fa (relative to the total for the three);
  D: 90% HCFO-1233zdZ, 5% HFO-1234zeE and 5% HFC-245fa (relative to the total for the three).

It is found that the composition has a boiling point of 0 to 40° C. for a pressure from 0.6 bar absolute to 8.6 bar absolute approximately.

The decantation ranges for a mixture comprising equal mass proportions of HCFO-1233zdZ, HFO-1234zeE and HFC-245fa are: from 5% to 80% HF at 0° C.; from 5% to 75% HF at 25° C.; and from 5% to 70% HF at 40° C.

Example 3—HF/HCFO-1233zdZ/HFO-1234zeZ/HFC-245fa Quaternary Composition

Azeotropic and hetero-azeotropic behavior was observed for the HF/HCFO-1233zdZ/HFO-1234zeZ/HFC-245fa quaternary mixture.

Figure 3:
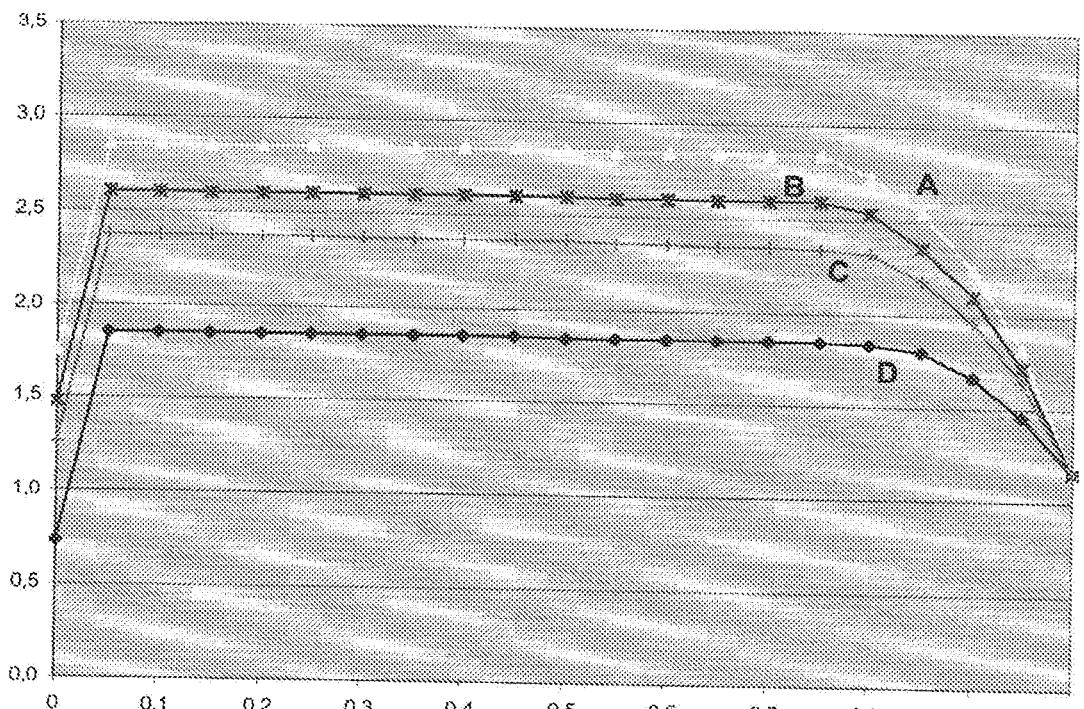
FIG. 3 represents the vapor pressure (on the y-axis, in bar absolute) of mixtures according to the invention in accordance with Example 3, for the 25° C. isotherm. The mass fraction of HF in the composition is given on the x-axis. Curves A, B, C and D correspond to various compositions of (hydro)halocarbon compounds (see Example 3).

FIG. 3 illustrates the azeotropic behavior for the isotherm at 25° C., for various HCFO-1233zdZ/HFO-1234zeZ/HFC-245fa proportions, namely:
  A: 5% HCFO-1233zdZ, 90% HFO-1234zeZ and 5% HFC-245fa (relative to the total for the three);
  B: 5% HCFO-1233zdZ, 5% HFO-1234zeZ and 90% HFC-245fa (relative to the total for the three);
  C: 40% HCFO-1233zdZ, 30% HFO-1234zeZ and 30% HFC-245fa (relative to the total for the three);
  D: 90% HCFO-1233zdZ, 5% HFO-1234zeZ and 5% HFC-245fa (relative to the total for the three).

It is found that the composition has a boiling point of 0 to 40° C. for a pressure from 0.6 bar absolute to 4.8 bar absolute approximately.

The decantation ranges for a mixture comprising equal mass proportions of HCFO-1233zdZ, HFO-1234zeZ and HFC-245fa are: from 5% to 80% HF at 0° C.; from 5% to 75% HF at 25° C.; and from 5% to 75% HF at 40° C.

Example 4—HF/HCFO-1233zdE/HCFO-1233zdZ/HFC-245fa Quaternary Composition

Azeotropic and hetero-azeotropic behavior was observed for the HF/HCFO-1233zdE/HCFO-1233zdZ/HFC-245fa quaternary mixture.

Figure 4:
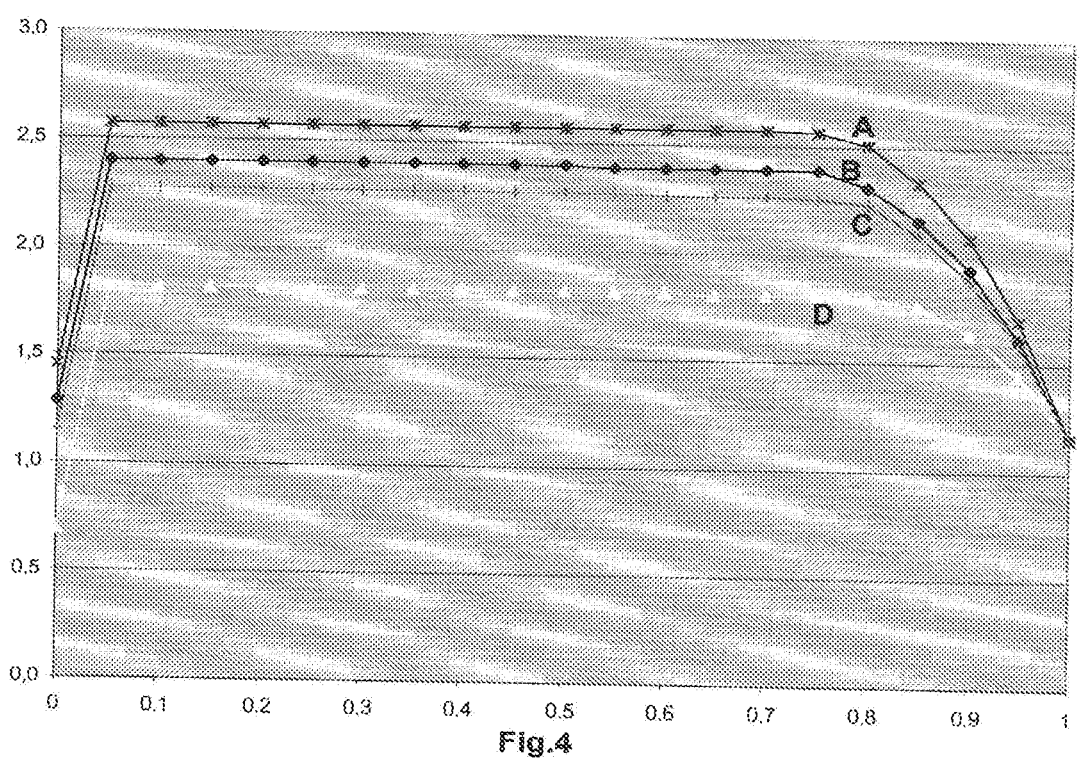
FIG. 4 represents the vapor pressure (on the y-axis, in bar absolute) of mixtures according to the invention in accordance with Example 4, for the 25° C. isotherm. The mass fraction of HF in the composition is given on the x-axis. Curves A, B, C and D correspond to various compositions of (hydro)halocarbon compounds (see Example 4).

FIG. 4 illustrates the azeotropic behavior for the isotherm at 25° C., for various HCFO-1233zdE/HCFO-1233zdZ/HFC-245fa proportions, namely:
  A: 5% HCFO-1233zdE, 5% HCFO-1233zdZ and 90% HFC-245fa (relative to the total for the three);
  B: 90% HCFO-1233zdE, 5% HCFO-1233zdZ and 5% HFC-245fa (relative to the total for the three);
  C: 40% HCFO-1233zdE, 30% HCFO-1233zdZ and 30% HFC-245fa (relative to the total for the three);
  D: 5% HCFO-1233zdE, 90% HCFO-1233zdZ and 5% HFC-245fa (relative to the total for the three).

It is found that the composition has a boiling point of 0 to 40° C. for a pressure from 0.6 bar absolute to 4.4 bar absolute approximately.

The decantation ranges for a mixture comprising equal mass proportions of HCFO-1233zdE, HCFO-1233zdZ and HFC-245fa are: from 5% to 80% HF at 0° C.; from 5% to 75% HF at 25° C.; and from 5% to 75% HF at 40° C.

Example 5—HF/HCFO-1233zdZ/HFO-1234zeE/HFO-1234zeZ/HFC-245fa Quinternary Composition Azeotropic and hetero-azeotropic behavior was observed for the HF/HCFO-1233zdZ/HFO-1234zeE/HFO-1234zeZ/HFC-245fa quinternary mixture.

Figure 5:
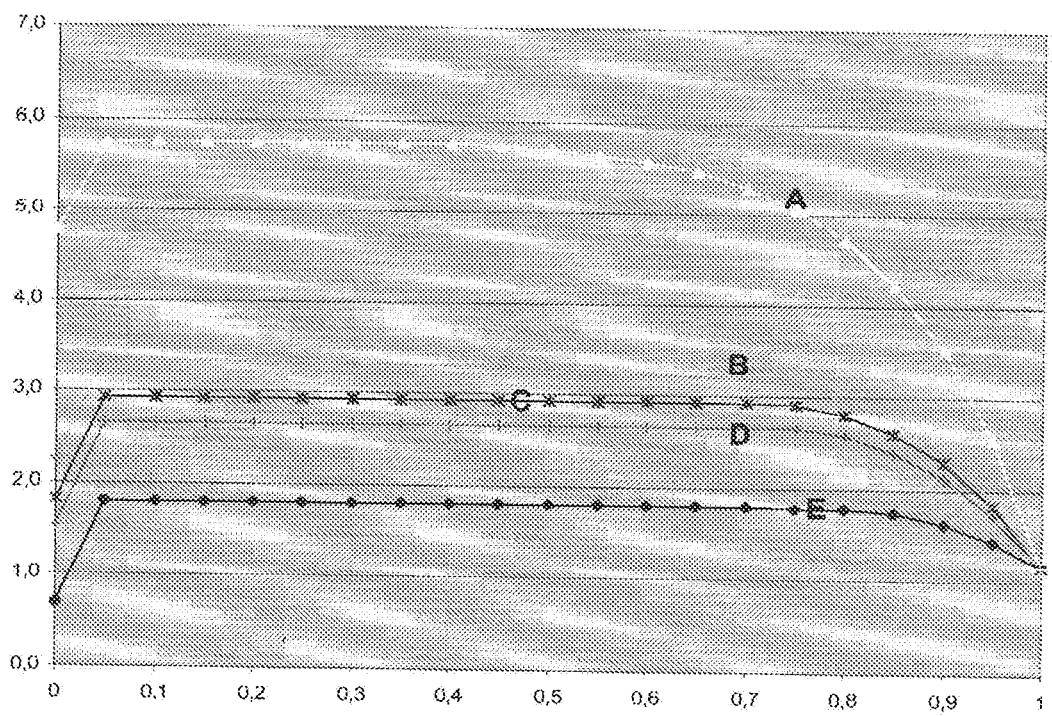
FIG. 5 represents the vapor pressure (on the y-axis, in bar absolute) of mixtures according to the invention in accordance with Example 5, for the 25° C. isotherm. The mass fraction of HF in the composition is given on the x-axis. Curves A, B, C, D and E correspond to various compositions of (hydro)halocarbon compounds (see Example 5).

FIG. 5 illustrates the azeotropic behavior for the isotherm at 25° C., for various HCFO-1233zdZ/HFO-1234zeE/HFO-1234zeZ/HFC-245fa proportions, namely:
  A: 1% HCFO-1233zdZ, 97% HFO-1234zeE, 1% HFO-1234zeZ and 1% HFC-245fa (relative to the total for the four);
  B: 25% HCFO-1233zdZ, 25% HFO-1234zeE, 25% HFO-1234zeZ and 25% HFC-245fa (relative to the total for the four);
  C: 1% HCFO-1233zdZ, 1% HFO-1234zeE, 97% HFO-1234zeZ and 1% HFC-245fa (relative to the total for the four);
  D: 1% HCFO-1233zdZ, 1% HFO-1234zeE, 1% HFO-1234zeZ and 97% HFC-245fa (relative to the total for the four);
  E: 97% HCFO-1233zdZ, 1% HFO-1234zeE, 1% HFO-1234zeZ and 1% HFC-245fa (relative to the total for the four).

It is found that the composition has a boiling point of 0 to 40° C. for a pressure from 0.6 bar absolute to 8.9 bar absolute approximately.

The decantation ranges for a mixture comprising equal mass proportions of HCFO-1233zdZ, HFO-1234zeE, HFO-1234zeZ and HFC-245fa are: from 5% to 80% HF at 0° C.; from 5% to 75% HF at 25° C.; and from 5% to 65% HF at 40° C.

Example 6—HF/HCFO-1233zdE/HCFO-1233zdZ/HFO-1234zeE/HFC-245fa Quinternary Composition Azeotropic and hetero-azeotropic behavior was observed for the HF/HCFO-1233zdE/HCFO-1233zdZ/HFO-1234zeE/HFC-245fa quinternary mixture.

Figure 6:
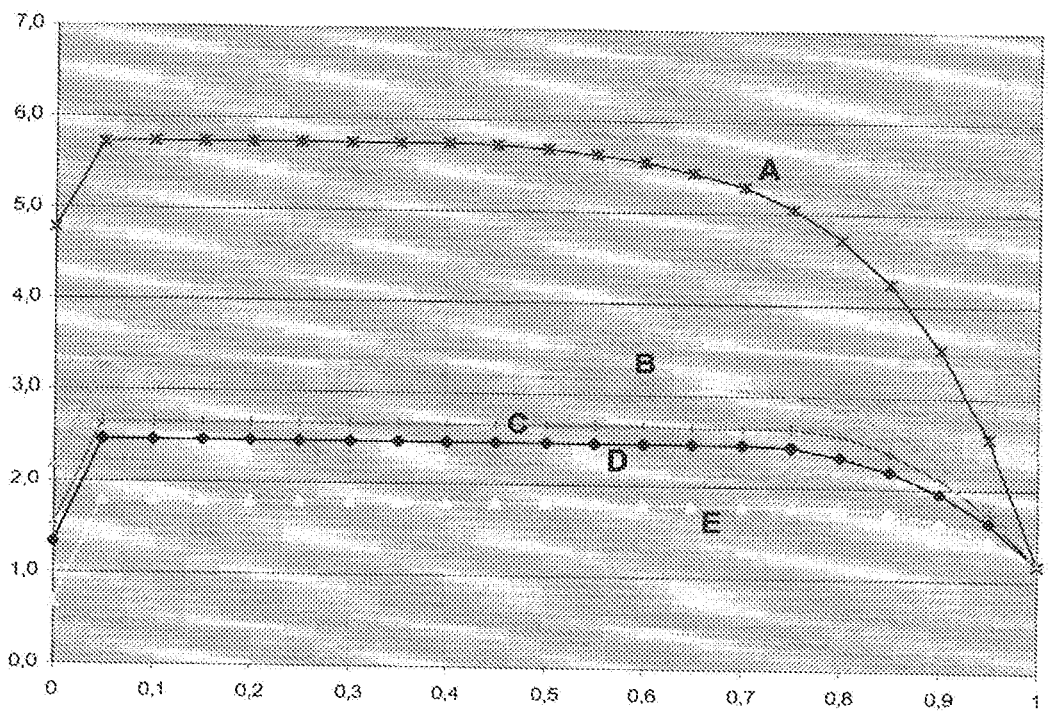
FIG. 6 represents the vapor pressure (on the y-axis, in bar absolute) of mixtures according to the invention in accordance with Example 6, for the 25° C. isotherm. The mass fraction of HF in the composition is given on the x-axis. Curves A, B, C, D and E correspond to various compositions of (hydro)halocarbon compounds (see Example 6).

FIG. 6 illustrates the azeotropic behavior for the isotherm at 25° C., for various HCFO-1233zdE/HCFO-1233zdZ/HFO-1234zeE/HFC-245fa proportions, namely:
  A: 1% HCFO-1233zdE, 1% HCFO-1233zdZ, 97% HFO-1234zeE and 1% HFC-245fa (relative to the total for the four);
  B: 25% HCFO-1233zdE, 25% HCFO-1233zdZ, 25% HFO-1234zeE and 25% HFC-245fa (relative to the total for the four);
  C: 1% HCFO-1233zdE, 1% HCFO-1233zdZ, 1% HFO-1234zeE and 97% HFC-245fa (relative to the total for the four);
  D: 97% HCFO-1233zdE, 1% HCFO-1233zdZ, 1% HFO-1234zeE and 1% HFC-245fa (relative to the total for the four);
  E: 1% HCFO-1233zdE, 97% HCFO-1233zdZ, 1% HFO-1234zeE and 1% HFC-245fa (relative to the total for the four).

It is found that the composition has a boiling point of 0 to 40° C. for a pressure from 0.6 bar absolute to 8.9 bar absolute approximately.

The decantation ranges for a mixture comprising equal mass proportions of HCFO-1233zdE, HCFO-1233zdZ, HFO-1234zeE and HFC-245fa are: from 5% to 80% HF at 0° C.; from 5% to 75% HF at 25° C.; and from 5% to 65% HF at 40° C.

Example 7—HF/HCFO-1233zdE/HCFO-1233zdZ/HFO-1234zeZ/HFC-245fa Quinternary Composition Azeotropic and hetero-azeotropic behavior was observed for the HF/HCFO-1233zdE/HCFO-1233zdZ/HFO-1234zeZ/HFC-245fa quinternary mixture.

Figure 7:
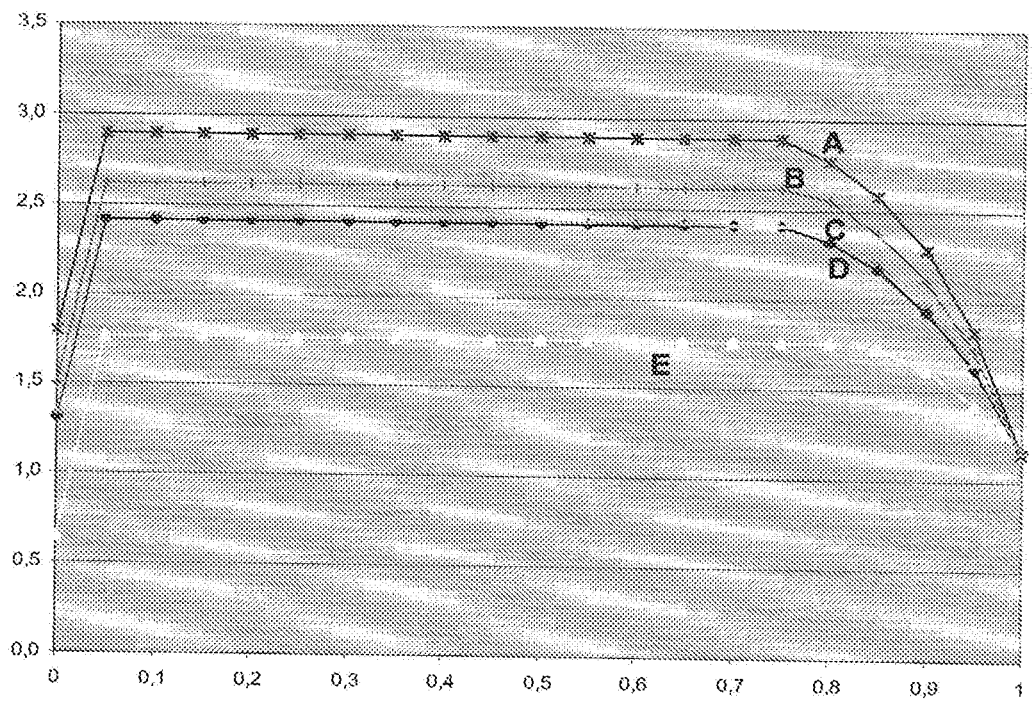
FIG. 7 represents the vapor pressure (on the y-axis, in bar absolute) of mixtures according to the invention in accordance with Example 7, for the 25° C. isotherm. The mass fraction of HF in the composition is given on the x-axis. Curves A, B, C, D and E correspond to various compositions of (hydro)halocarbon compounds (see Example 7).

FIG. 7 illustrates the azeotropic behavior for the isotherm at 25° C., for various HCFO-1233zdE/HCFO-1233zdZ/HFO-1234zeZ/HFC-245fa proportions, namely:
  A: 1% HCFO-1233zdE, 1% HCFO-1233zdZ, 97% HFO-1234zeZ and 1% HFC-245fa (relative to the total for B: 1% HCFO-1233zdE, 1% HCFO-1233zdZ, 1% HFO-1234zeZ and 97% HFC-245fa (relative to the total for the four);

C: 25% HCFO-1233zdE, 25% HCFO-1233zdZ, 25% HFO-1234zeZ and 25% HFC-245fa (relative to the total for the four);

D: 97% HCFO-1233zdE, 1% HCFO-1233zdZ, 1% HFO-1234zeZ and 1% HFC-245fa (relative to the total for the four);

E: 1% HCFO-1233zdE, 97% HCFO-1233zdZ, 1% HFO-1234zeZ and 1% HFC-245fa (relative to the total for the four).

It is found that the composition has a boiling point of 0 to 40° C. for a pressure from 0.6 bar absolute to 4.8 bar absolute approximately.

The decantation ranges for a mixture comprising equal mass proportions of HCFO-1233zdE, HCFO-1233zdZ, HFO-1234zeZ and HFC-245fa are: from 5% to 80% HF at 0° C.; from 5% to 75% HF at 25° C.; and from 5% to 70% HF at 40° C.

Example 8—HF/HCFO-1233zdE/HCFO-1233zdZ/ HFO-1234zeE/HFO-1234zeZ/HFC-245fa Senary Composition Azeotropic and hetero-azeotropic behavior was observed for the HF/HCFO-1233zdE/HCFO-1233zdZ/HFO-1234zeE/HFO-1234zeZ/HFC-245fa senary mixture.

Figure 8:
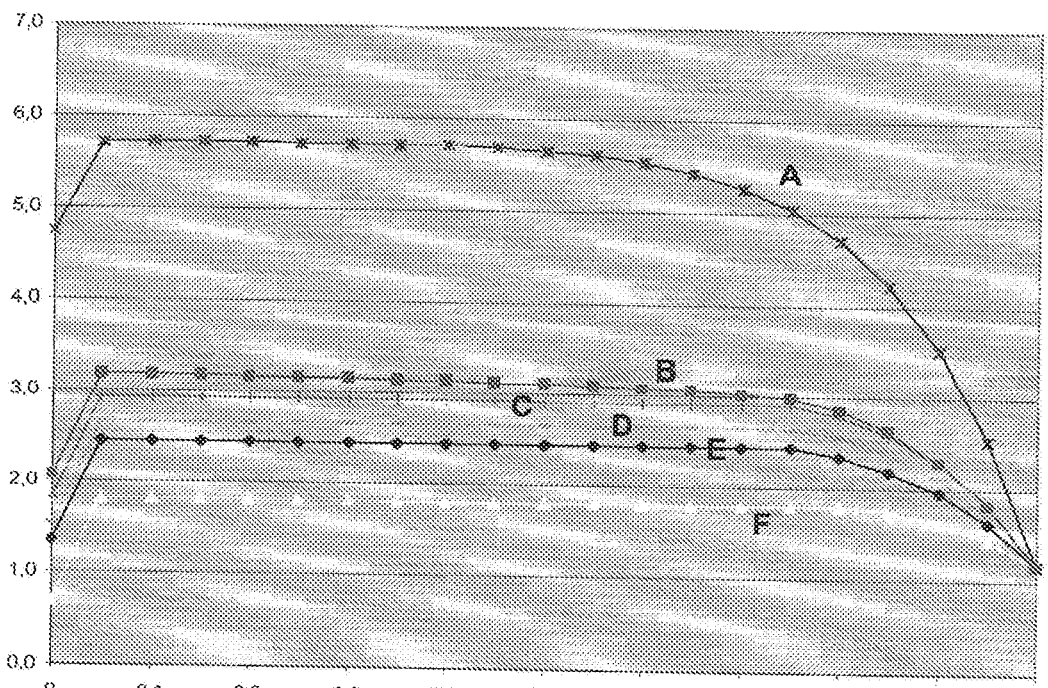
FIG. 8 represents the vapor pressure (on the y-axis, in bar absolute) of mixtures according to the invention in accordance with Example 8, for the 25° C. isotherm. The mass fraction of HF in the composition is given on the x-axis.

FIG. 8 illustrates the azeotropic behavior for the isotherm at 25° C., for various HCFO-1233zdE/HCFO-1233zdZ/HFO-1234zeE/HFO-1234zeZ/HFC-245fa proportions, namely:

A: 1% HCFO-1233zdE, 1% HCFO-1233zdZ, 96% HFO-1234zeE, 1% HFO-1234zeZ and 1% HFC-245fa (relative to the total for the five);

B: 20% HCFO-1233zdE, 20% HCFO-1233zdZ, 20% HFO-1234zeE, 20% HFO-1234zeZ and 20% HFC-245fa (relative to the total for the five);

C: 1% HCFO-1233zdE, 1% HCFO-1233zdZ, 1% HFO-1234zeE, 96% HFO-1234zeZ and 1% HFC-245fa (relative to the total for the five);

D: 1% HCFO-1233zdE, 1% HCFO-1233zdZ, 1% HFO-1234zeE, 1% HFO-1234zeZ and 96% HFC-245fa (relative to the total for the five);

E: 96% HCFO-1233zdE, 1% HCFO-1233zdZ, 1% HFO-1234zeE, 1% HFO-1234zeZ and 1% HFC-245fa (relative to the total for the five);

F: 1% HCFO-1233zdE, 96% HCFO-1233zdZ, 1% HFO-1234zeE, 1% HFO-1234zeZ and 1% HFC-245fa (relative to the total for the five).

It is found that the composition has a boiling point of 0 to 40° C. for a pressure from 0.6 bar absolute to 8.8 bar absolute approximately.

The decantation ranges for a mixture comprising equal mass proportions of HCFO-1233zdE, HCFO-1233zdZ, HFO-1234zeE, HFO-1234zeZ and HFC-245fa are: from 5% to 80% HF at 0° C.; from 5% to 75% HF at 25° C.; and from 5% to 65% HF at 40° C.

Embodiments

1. An azeotropic or quasi-azeotropic composition comprising hydrogen fluoride, Z-3,3,3-trifluoro-1-chloropropene and one or more (hydro)halocarbon compounds comprising from 1 to 3 carbon atoms.

2. The composition as in embodiment 1, in which the (hydro)halocarbon compound(s) comprise three carbon atoms, and are preferably chosen from propanes and propenes that are partially or totally substituted with halogens.

3. The composition as in embodiment(s) 1 or 2, in which the (hydro)halocarbon compound(s) are chosen from tetrachlorofluoropropanes, trichlorodifluoropropanes, dichlorotrifluoropropanes, chlorotetrafluoropropanes, pentafluoropropanes, dichlorodifluoropropenes, trichlorofluoropropenes, chlorotrifluoropropenes and tetrafluoropropenes.

4. The composition as in one of embodiments 1 to 3, comprising hydrogen fluoride, Z-3,3,3-trifluoro-1-chloropropene, E-3,3,3-trifluoro-1-chloropropene and one or more other (hydro)halocarbon compounds comprising from 1 to 3 carbon atoms.

5. The composition as in one of embodiments 1 to 4, comprising hydrogen fluoride, Z-3,3,3-trifluoro-1-chloropropene, E-1,3,3,3-tetrafluoropropene and one or more other (hydro)halocarbon compounds comprising from 1 to 3 carbon atoms.

6. The composition as in one of embodiments 1 to 5, comprising hydrogen fluoride, Z-3,3,3-trifluoro-1-chloropropene, Z-1,3,3,3-tetrafluoropropene and one or more other (hydro)halocarbon compounds comprising from 1 to 3 carbon atoms.

7. The composition as in one of embodiments 1 to 6, comprising hydrogen fluoride, Z-3,3,3-trifluoro-1-chloropropene, 1,1,1,3,3-pentafluoropropane and one or more other (hydro)halocarbon compounds comprising from 1 to 3 carbon atoms.

8. The composition as in one of embodiments 1 to 7, which is a ternary mixture, and is preferably a mixture of hydrogen fluoride, Z-3,3,3-trifluoro-1-chloropropene and E-3,3,3-trifluoro-1-chloropropene.

9. The composition as in one of embodiments 1 to 7, which is a quaternary mixture, and is preferably a mixture of:

hydrogen fluoride, Z-3,3,3-trifluoro-1-chloropropene, E-3,3,3-trifluoro-1-chloropropene and 1,1,1,3,3-pentafluoropropane; or hydrogen fluoride, Z-3,3,3-trifluoro-1-chloropropene, E-1,3,3,3-tetrafluoropropene and 1,1,1,3,3-pentafluoropropane; or hydrogen fluoride, Z-3,3,3-trifluoro-1-chloropropene, Z-1,3,3,3-tetrafluoropropene and 1,1,1,3,3-pentafluoropropane.

10. The composition as in one of embodiments 1 to 7, which is a quinternary mixture, and is preferably a mixture of:

hydrogen fluoride, Z-3,3,3-trifluoro-1-chloropropene, E-3,3,3-trifluoro-1-chloropropene, Z-1,3,3,3-tetrafluoropropene and 1,1,1,3,3-pentafluoropropane; or hydrogen fluoride, Z-3,3,3-trifluoro-1-chloropropene, E-3,3,3-trifluoro-1-chloropropene, E-1,3,3,3-tetrafluoropropene and 1,1,1,3,3-pentafluoropropane; or hydrogen fluoride, Z-3,3,3-trifluoro-1-chloropropene, Z-1,3,3,3-tetrafluoropropene, E-1,3,3,3-tetrafluoropropene and 1,1,1,3,3-pentafluoropropane.

11. The composition as in one of embodiments 1 to 7, which is a senary mixture, and is preferably a mixture of:

hydrogen fluoride, Z-3,3,3-trifluoro-1-chloropropene, E-3,3,3-trifluoro-1-chloropropene, Z-1,3,3,3-tetrafluoropropene, E-1,3,3,3-tetrafluoropropene and 1,1,1,3,3-pentafluoropropane.

12. The composition as in one of embodiments 1 to 11, which is hetero-azeotropic or quasi-hetero-azeotropic.

13. The composition as in one of embodiments 1 to 12, which comprises from 1% to 85% by weight, preferably from 1% to 80% by weight, more particularly preferably from 5% to 80% by weight and most particularly preferably from 5% to 75% by weight of hydrogen fluoride; and/or from 15% to 99% by weight, preferably from 20% to 99% by weight, more particularly preferably from 20% to 95% by weight and most particularly preferably from 25% to 95% by weight of (hydro)halocarbon compounds comprising from 1 to 3 carbon atoms.

14. The composition as in one of embodiments 1 to 13, which has a boiling point of 0 to 40° C. for a pressure from 0.5 to 9 bar absolute.

15. A process for producing a main (hydro)halocarbon compound, comprising:
the formation of a mixture of compounds comprising hydrogen fluoride, Z-3,3,3-trifluoro-1-chloropropene and one or more other (hydro)halocarbon compounds;
distillation of this mixture making it possible to collect, firstly, an azeotropic composition as in one of embodiments 1 to 14, and, secondly, at least one of the compounds of the mixture.

16. The process as in embodiment 15, in which distillation makes it possible to collect, firstly, an azeotropic composition as in one of embodiments 1 to 14, and, secondly, hydrogen fluoride; or alternatively, firstly, an azeotropic composition as in one of embodiments 1 to 14, and, secondly, E-3,3,3-trifluoro-1-chloropropene.

17. The process as in embodiment 15 or 16, which is a process for producing 3,3,3-trifluoro-1-chloropropene, and preferably E-3,3,3-trifluoro-1-chloropropene.

18. The process as in one of embodiments 15 to 17, in which the mixture of compounds is obtained after a fluorination step, comprising the reaction of a chloro compound with hydrogen fluoride.

19. The process as in one of embodiments 15 to 18, in which the azeotropic composition collected is separated, preferably by decantation, into two immiscible liquid fractions, namely a fraction rich in hydrogen fluoride and a fraction poor in hydrogen fluoride, the fraction rich in hydrogen fluoride containing a higher proportion of hydrogen fluoride than the fraction poor in hydrogen fluoride; and the fraction rich in hydrogen fluoride being, where appropriate, recycled into the fluorination step.

20. The process as in one of embodiments 15 to 19, in which the chloro compound is 1,1,1,3,3-pentachloropropane or 1,1,3,3-tetrachloropropene.

The invention claimed is:
1. A process for producing a (hydro)halocarbon compound comprising from 1 to 3 carbon atoms, comprising:
forming a mixture of compounds comprising hydrogen fluoride, Z-3,3,3-trifluoro-1-chloropropene and two or more (hydro)halocarbon compounds comprising from 1 to 3 carbon atoms;
distilling the mixture to, firstly, an azeotropic composition comprising hydrogen fluoride, Z-3,3,3-trifluoro-1-chloropropene and two or more (hydro)halocarbon compounds comprising from 1 to 3 carbon atoms, and, secondly, at least one of the compounds of the mixture.

2. The process as claimed in claim 1, comprising distilling the mixture to collect, firstly, the azeotropic composition, and, secondly, hydrogen fluoride.

3. The process as claimed in claim 1, comprising distilling the mixture to collect, firstly, the azeotropic composition, and, secondly, E-3,3,3-trifluoro-1-chloropropene.

4. The process as claimed in claim 1, wherein the at least one of the compounds of the mixture comprises 3,3,3-trifluoro-1-chloropropene.

5. The process as claimed in claim 1, wherein the at least one of the compounds of the mixture comprises E-3,3,3-trifluoro-1-chloropropene.

6. The process as claimed in claim 1, wherein the forming the mixture of compounds comprises a fluorination step, comprising the reaction of a chloro compound with hydrogen fluoride.

7. The process as claimed in claim 6, comprising separating the azeotropic composition into two immiscible liquid fractions, namely a fraction rich in hydrogen fluoride and a fraction poor in hydrogen fluoride, the fraction rich in hydrogen fluoride containing a higher proportion of hydrogen fluoride than the fraction poor in hydrogen fluoride; and the fraction rich in hydrogen fluoride being, where appropriate, recycled into the fluorination step.

8. The process as claimed in claim 7, comprising separating the azeotropic composition by decantation.

9. The process as claimed in claim 6, wherein the chloro compound is 1,1,1,3,3-pentachloropropane or 1,1,3,3-tetrachloropropene.

10. The process as claimed in claim 1, wherein the two or more (hydro)halocarbon compounds comprise three carbon atoms.

11. The process as claimed in claim 1, wherein the two or more (hydro)halocarbon compounds is selected from the group consisting of tetrachlorofluoropropanes, trichlorodifluoropropanes, dichlorotrifluoropropanes, chlorotetrafluoropropanes, pentafluoropropanes, dichlorodifluoropropenes, trichlorofluoropropenes, chlorotrifluoropropenes and tetrafluoropropenes.

* * * * *